(12) United States Patent
Strobl et al.

(10) Patent No.: US 9,265,926 B2
(45) Date of Patent: Feb. 23, 2016

(54) ELECTROSURGICAL DEVICES

(71) Applicant: Ethicon Endo-Surgery, Inc., Cincinnati, OH (US)

(72) Inventors: Geoffrey S. Strobl, Williamsburg, OH (US); Chad P. Boudreaux, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 21 days.

(21) Appl. No.: 14/075,839

(22) Filed: Nov. 8, 2013

(65) Prior Publication Data
US 2015/0133921 A1    May 14, 2015

(51) Int. Cl.
| A61B 18/14 | (2006.01) |
| A61N 1/00 | (2006.01) |
| A61B 17/3205 | (2006.01) |
| A61B 17/29 | (2006.01) |
| A61B 18/00 | (2006.01) |

(52) U.S. Cl.
CPC . *A61N 1/00* (2013.01); *A61B 17/29* (2013.01); *A61B 17/3205* (2013.01); *A61B 18/1445* (2013.01); *A61B 2017/2945* (2013.01); *A61B 2018/00083* (2013.01); *A61B 2018/00922* (2013.01); *A61B 2018/1432* (2013.01); *A61B 2018/1455* (2013.01)

(58) Field of Classification Search
CPC ............. A61B 18/1447; A61B 18/085; A61B 18/1445; A61B 2018/1455; A61B 2018/00607
USPC .................................................... 606/51, 52
See application file for complete search history.

(56) References Cited

U.S. PATENT DOCUMENTS

| 2,366,274 A | 1/1945 | Luth et al. |
| 2,458,152 A | 1/1949 | Eakins |
| 2,510,693 A | 6/1950 | Green |
| 3,166,971 A | 1/1965 | Stoecker |
| 3,580,841 A | 5/1971 | Cadotte et al. |

(Continued)

FOREIGN PATENT DOCUMENTS

| DE | 29623113 U1 | 10/1997 |
| DE | 20004812 U1 | 9/2000 |

(Continued)

OTHER PUBLICATIONS

U.S. Appl. No. 14/075,863, filed Nov. 8, 2013.

(Continued)

*Primary Examiner* — Michael Peffley
*Assistant Examiner* — Thomas Giuliani

(57) ABSTRACT

In one embodiment, a surgical instrument comprises a handle assembly. The handle assembly comprises a closure trigger defining an energy button hole, an energy button located within the energy button hole, and a firing trigger. A shaft assembly is coupled to the handle assembly and comprises an outer tube, a closure actuator coupled to the closure trigger, and a firing actuator operatively coupled to the firing trigger. An end effector is coupled to a distal end of the shaft assembly. The end effector comprises a jaw assembly having a proximal end and a distal end. The jaw assembly comprises a first and a second jaw member. The first and second jaw members define a longitudinal slot. The closure actuator is coupled to the first jaw member to pivotally move the first jaw member from an open position to a closed position. A cutting member is deployable within the longitudinal slot.

20 Claims, 33 Drawing Sheets

(56) References Cited

U.S. PATENT DOCUMENTS

| | | |
|---|---|---|
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,910,389 A | 3/1990 | Sherman et al. |
| 4,920,978 A | 5/1990 | Colvin |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,160,334 A | 11/1992 | Billings et al. |
| 5,190,541 A | 3/1993 | Abele et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,318,564 A | 6/1994 | Eggers |
| 5,318,589 A | 6/1994 | Lichtman |
| 5,330,471 A | 7/1994 | Eggers |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,364 A | 3/1995 | Anderhub et al. |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,542,916 A | 8/1996 | Hirsch et al. |
| 5,558,671 A | 9/1996 | Yates |
| 5,563,179 A | 10/1996 | Stone et al. |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,611,813 A | 3/1997 | Lichtman |
| 5,618,307 A | 4/1997 | Donlon et al. |
| 5,624,452 A | 4/1997 | Yates |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,713,896 A | 2/1998 | Nardella |
| 5,716,366 A | 2/1998 | Yates |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,138 A | 8/1998 | Shipp |
| 5,797,941 A | 8/1998 | Schulze et al. |
| 5,800,432 A | 9/1998 | Swanson |
| 5,800,449 A | 9/1998 | Wales |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,836,909 A | 11/1998 | Cosmescu |
| 5,836,943 A | 11/1998 | Miller, III |
| 5,853,412 A | 12/1998 | Mayenberger |
| 5,876,401 A | 3/1999 | Schulze et al. |
| 5,880,668 A | 3/1999 | Hall |
| 5,891,142 A | 4/1999 | Eggers et al. |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,144,402 A | 11/2000 | Norsworthy et al. |
| 6,152,923 A | 11/2000 | Ryan |
| 6,174,309 B1 | 1/2001 | Wrublewski et al. |
| 6,206,876 B1 | 3/2001 | Levine et al. |
| 6,228,080 B1 | 5/2001 | Gines |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,702 B2 | 10/2002 | Schulze et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |

(56) References Cited

U.S. PATENT DOCUMENTS

| | | |
|---|---|---|
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |
| 7,879,070 B2 | 2/2011 | Ortiz et al. |

(56) References Cited

U.S. PATENT DOCUMENTS

| | | |
|---|---|---|
| 7,901,400 B2 | 3/2011 | Wham et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,221,415 B2 | 7/2012 | Francischelli |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,888,776 B2 | 11/2014 | Dietz et al. |
| 8,906,016 B2 | 12/2014 | Boudreaux et al. |
| 8,926,607 B2 | 1/2015 | Norvell et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,986,302 B2 | 3/2015 | Aldridge et al. |
| 9,005,199 B2 | 4/2015 | Beckman et al. |
| 9,011,437 B2 | 4/2015 | Woodruff et al. |
| 9,044,243 B2 | 6/2015 | Johnson et al. |
| 2002/0022836 A1 | 2/2002 | Goble et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1* | 1/2008 | Odom ............... A61B 18/1445 606/51 |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |
| 2009/0012520 A1* | 1/2009 | Hixson et al. .................. 606/51 |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082768 A1* | 3/2009 | Bacher et al. .................. 606/51 |
| 2009/0099582 A1 | 4/2009 | Isaacs et al. |
| 2009/0125026 A1 | 5/2009 | Rioux et al. |
| 2009/0125027 A1 | 5/2009 | Fischer |

(56) References Cited

U.S. PATENT DOCUMENTS

| | | |
|---|---|---|
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0320268 A1 | 12/2009 | Cunningham et al. |
| 2009/0326530 A1 | 12/2009 | Orban et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0145334 A1* | 6/2010 | Olson et al. ................ 606/48 |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1* | 4/2011 | Felder ............... A61B 18/1445 606/42 |
| 2011/0155781 A1 | 6/2011 | Swensgard et al. |
| 2011/0224668 A1 | 9/2011 | Johnson et al. |
| 2011/0276049 A1* | 11/2011 | Gerhardt ..................... 606/45 |
| 2011/0276057 A1 | 11/2011 | Conlon et al. |
| 2011/0301605 A1 | 12/2011 | Horner |
| 2011/0306967 A1 | 12/2011 | Payne et al. |
| 2012/0010616 A1 | 1/2012 | Huang et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022527 A1 | 1/2012 | Woodruff et al. |
| 2012/0078244 A1* | 3/2012 | Worrell ............ A61B 17/07207 606/33 |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116379 A1* | 5/2012 | Yates et al. ................. 606/33 |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0265196 A1 | 10/2012 | Turner et al. |
| 2013/0023875 A1 | 1/2013 | Harris et al. |
| 2013/0030433 A1 | 1/2013 | Heard |
| 2013/0079762 A1 | 3/2013 | Twomey et al. |
| 2013/0085496 A1* | 4/2013 | Unger ............... A61B 18/1445 606/45 |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2508143 B1 | 2/2014 |
| GB | 2472216 A | 2/2011 |
| JP | H 08-229050 A | 9/1996 |
| JP | 2008-018226 A | 1/2008 |
| WO | WO 93/07817 | 4/1993 |
| WO | WO 93/22973 A1 | 11/1993 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |

(56) References Cited

FOREIGN PATENT DOCUMENTS

| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2013/034629 A1 | 3/2013 |
| WO | WO 2013/062978 A2 | 5/2013 |

OTHER PUBLICATIONS

International Search Report for PCT/US2014/064053, Feb. 2, 2015 (5 pages).

Written Opinion for PCT/US2014/064053, Feb. 2, 2015 (6 pages).

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Covidien Brochure, The LigaSure Precise™ Instrument, dated Mar. 2011 (2 pages).

Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.

Jang, J. et al. "Neuro-fuzzy and Soft Computing." Prentice Hall, 1997, pp. 13-89, 199-293, 335-393,453-496, 535-549.

Douglas, S.C. "Introduction to Adaptive Filter". Digital Signal Processing Handbook. Ed. Vijay K. Madisetti and Douglas B. Williams. Boca Raton: CRC Press LLC, 1999.

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Sullivan, "Optimal Choice for Number of Strands in a Litz-Wire Transformer Winding," IEEE Transactions on Power Electronics, vol. 14, No. 2, Mar. 1999, pp. 283-291.

U.S. Appl. No. 14/218,558, filed Mar. 18, 2014.
U.S. Appl. No. 14/227,699, filed Mar. 27, 2014.
U.S. Appl. No. 14/227,708, filed Mar. 27, 2014.
U.S. Appl. No. 14/032,391, filed Sep. 20, 2013.

* cited by examiner

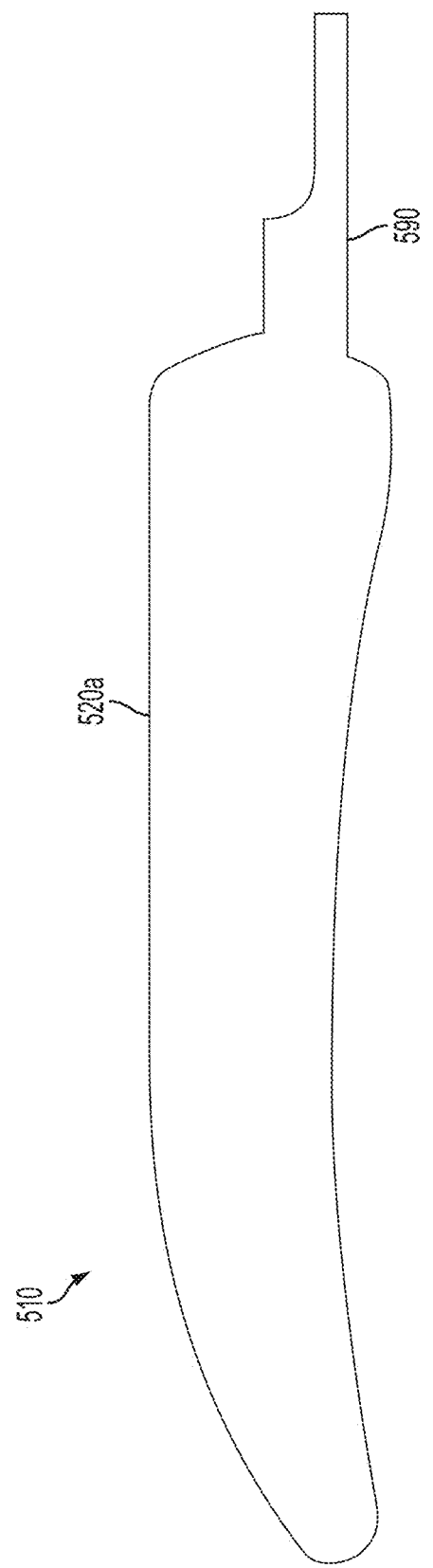

ELECTROSURGICAL DEVICES

CROSS-REFERENCE TO RELATED APPLICATIONS

This application is related to U.S. patent application Ser. No. 14/075,863, entitled ELECTROSURGICAL DEVICES, filed Nov. 8, 2013. now U.S. Patent Application Publication No. 2015/0133915, filed concurrently with the present application and incorporated by reference herein in its entirety.

BACKGROUND

The present disclosure is related generally to electrosurgical devices with various mechanisms for clamping and treating tissue. In particular, the present disclosure is related to electrosurgical devices with various mechanisms for controlling a curved end effector.

While several devices have been made and used, it is believed that no one prior to the inventors has made or used the device described in the appended claims.

SUMMARY

In various embodiments, a surgical instrument is disclosed. In one embodiment, the surgical instrument comprises a handle assembly, a shaft assembly, and an end effector. The handle assembly comprises a closure trigger defining an energy button hole, an energy button located within the energy button hole, and a firing trigger. The shaft assembly is coupled to the handle assembly. The shaft assembly comprises an outer tube, a closure actuator operatively coupled to the closure trigger, and a firing actuator operatively coupled to the firing trigger. The end effector is coupled to a distal end of the shaft assembly. The end effector comprises a jaw assembly having a proximal end and a distal end. The jaw assembly comprises a first jaw member and a second jaw member. The first and second jaw members define a longitudinal slot. The closure actuator is coupled to the first jaw member to pivotally move the first jaw member from an open position to a closed position relative to the second jaw member. A cutting member is deployable within the longitudinal slot. The cutting member is coupled to the firing actuator to advance the cutting member distally within the longitudinal slot.

In various embodiments, a surgical instrument is disclosed. In one embodiment, the surgical instrument comprises a handle assembly, a shaft assembly, and an end effector. The handle assembly comprises a closure trigger defining an energy button hole, an energy button located within the energy button hole, and a firing trigger. The shaft assembly is coupled to the handle assembly. The shaft assembly comprises an outer tube, a closure actuator operatively coupled to the closure trigger, and a firing actuator operatively coupled to the firing trigger. The end effector coupled to a distal end of the shaft assembly. The end effector comprises a jaw assembly having a proximal end and a distal end. The jaw assembly comprises a moveable jaw member and a fixed jaw member. The moveable jaw member is pivotably moveable between an open position and a closed position with respect to the fixed jaw member. In the closed position, the jaw assembly defines a radius of curvature. A cutting member is deployable within the curved slot. The cutting member is coupled to the firing actuator to advance the cutting member distally within the curved slot.

In various embodiments, a surgical instrument is disclosed. In one embodiment, the surgical instrument comprises a handle assembly. The handle assembly comprises a closure trigger defining an energy button hole, an energy button located within the energy button hole, and a firing trigger. A shaft assembly is coupled to the handle assembly. The shaft assembly comprises an outer tube, a closure actuator operatively coupled to the closure trigger, and a firing actuator operatively coupled to the firing trigger. An end effector is coupled to a distal end of the shaft assembly, the end effector comprises a jaw assembly having a proximal end and a distal end. The jaw assembly comprises a moveable jaw member and a fixed jaw member. The moveable jaw member is pivotably moveable between an open position and a closed position with respect to the fixed jaw member. The closure actuator is asymmetrically coupled to the moveable jaw member on a first side of a central axis of the shaft assembly. A pivot connection between the moveable jaw member and the fixed jaw member is offset to the first side of the central axis of the shaft assembly. In the closed position, the jaw assembly defines a radius of curvature and a smooth taper from the proximal end to the distal end.

DRAWINGS

The novel features of the embodiments described herein are set forth with particularity in the appended claims. The embodiments, however, both as to organization and methods of operation may be better understood by reference to the following description, taken in conjunction with the accompanying drawings as follows.

FIG. 28 illustrates one embodiment of the electrosurgical end effector of FIGS. 27A-27B comprising an off-set jaw closure actuator.

DESCRIPTION

Figure 1:
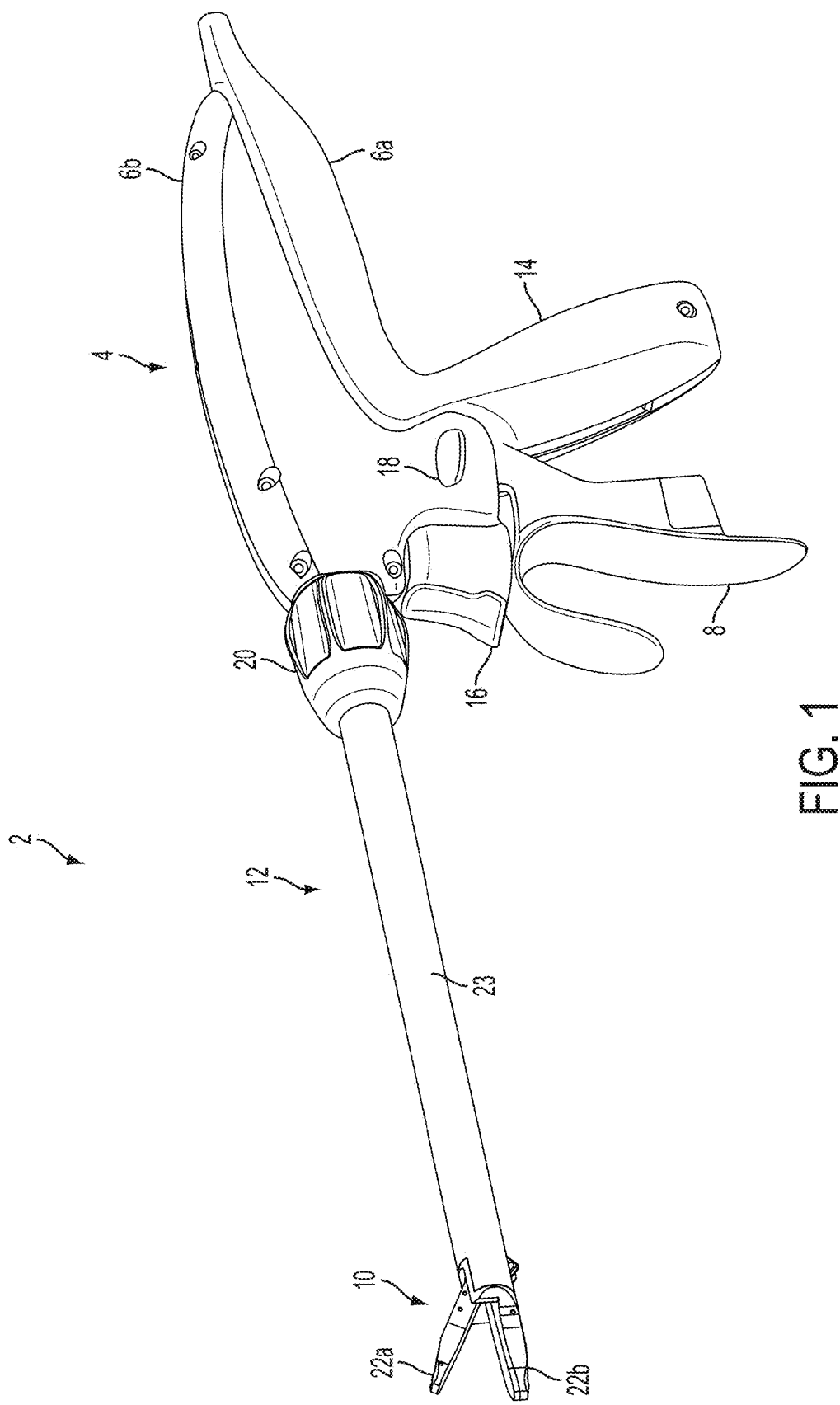
FIG. 1 illustrates one embodiment of an electrosurgical instrument.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the surgical devices with close quarter articulation features in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices with close quarter articulation features disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Turning now to the figures, FIG. 1 illustrates one embodiment of an electrosurgical instrument 2. The electrosurgical instrument 2 comprises a two-trigger clamp and cut mechanism. The electrosurgical instrument 2 comprises a handle assembly 4, a shaft assembly 12 coupled to a distal end of the handle assembly 4, and an end effector 10 coupled to the distal end of the shaft assembly 12. The handle assembly 4 is configured as a pistol grip and comprises left and right handle housing shrouds 6a, 6b, a closure trigger 8, a pistol-grip handle 14, a firing trigger 16, an energy button 18, and a rotatable shaft knob 20. An electrical cable 21 enters the handle assembly 4 at a proximal end.

The shaft assembly 12 comprises a jaw actuator, a cutting member actuator, and an outer sheath 23. The jaw actuator is operatively coupled to the closure trigger 8 of the handle assembly 4. In some embodiments, the outer sheath 23 comprises the jaw actuator. The cutting member actuator is operatively coupled to the firing trigger 14 of the handle assembly 4. The outer sheath 23 comprises one or more contact electrodes on the distal end configured to interface with the end effector 10. The one or more contact electrodes are operatively coupled to the energy button 18 and an energy source (not shown).

The energy source may be suitable for therapeutic tissue treatment, tissue cauterization/sealing, as well as sub-therapeutic treatment and measurement. The energy button 18 controls the delivery of energy to the electrode. A detailed explanation of each of these control elements is provided herein below. As used throughout this disclosure, a button refers to a switch mechanism for controlling some aspect of a machine or a process. The buttons may be made out of a hard material such as usually plastic or metal. The surface may be formed or shaped to accommodate the human finger or hand, so as to be easily depressed or pushed. Buttons can be most often biased switches, though even many un-biased buttons (due to their physical nature) require a spring to return to their un-pushed state. Terms for the "pushing" of the button, may include press, depress, mash, and punch.

In some embodiments, an end effector 10 is coupled to the distal end of the shaft assembly 12. The end effector 10 comprises a first jaw member 22a and a second jaw member 22b. The first jaw member 22a is pivotably coupled to the second jaw member 22b. The first jaw member 22a is pivotally moveable with respect to the second jaw member 22b to grasp tissue therebetween. In some embodiments, the second jaw member 22b is fixed. In other embodiments, the first jaw member 22a and the second jaw member 22b are pivotally movable. The end effector 10 comprises at least one electrode 92. The electrode 92 is configured to delivery energy. Energy delivered by the electrode 92 may comprise, for example, radiofrequency (RF) energy, sub-therapeutic RF energy, ultrasonic energy, and/or other suitable forms of energy. In some embodiments, a cutting member (not shown) is receivable within a longitudinal slot defined by the first jaw member 22a and/or the second jaw member 22b. The cutting member is configured to cut tissue grasped between the first jaw member 22a and the second jaw member 22b. In some embodiments, the cutting member comprises an electrode for delivering energy, such as, for example, RF and/or ultrasonic energy.

Figure 2:
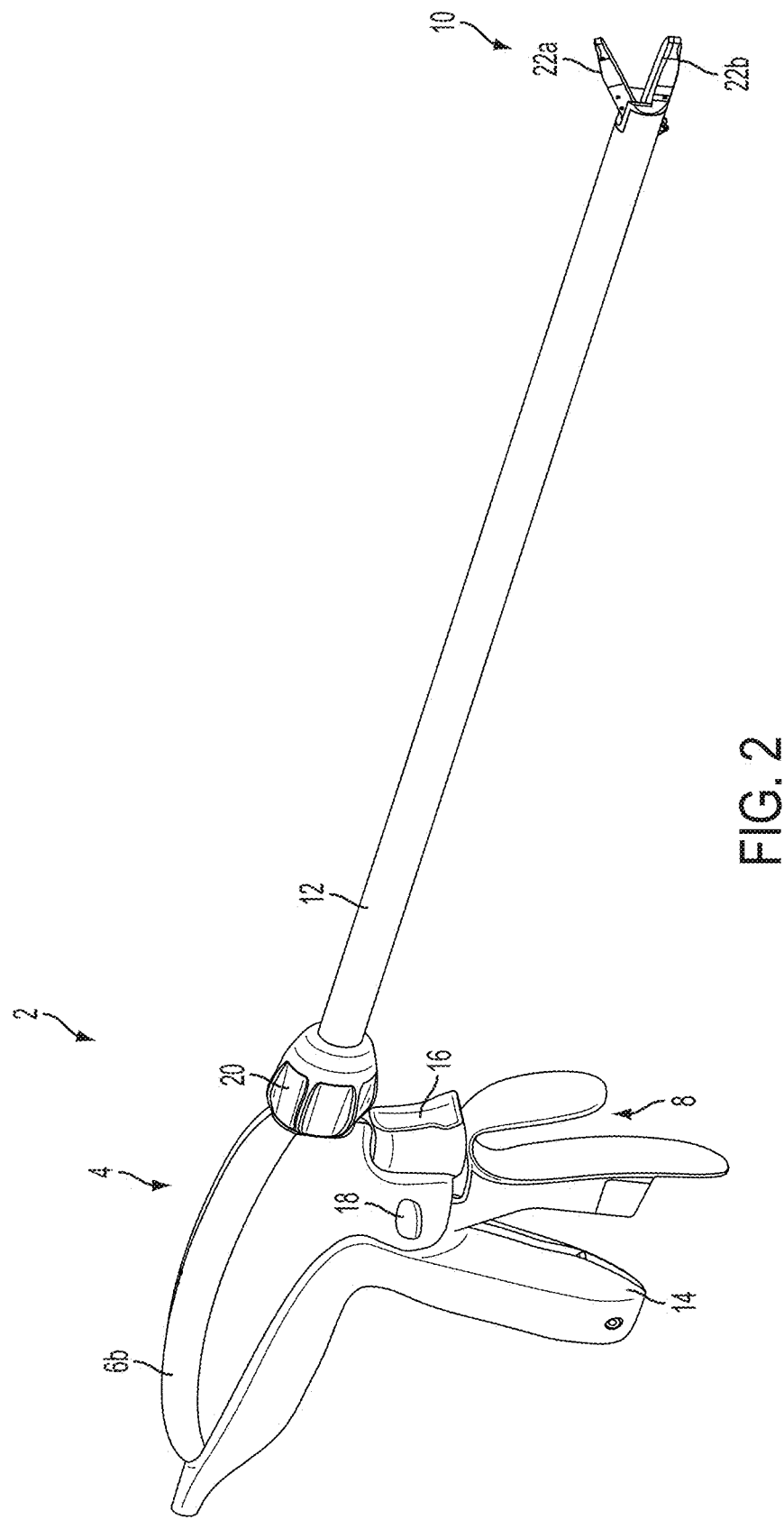
FIG. 2 illustrates a side-perspective of the electrosurgical instrument of FIG. 1.
Figure 3:
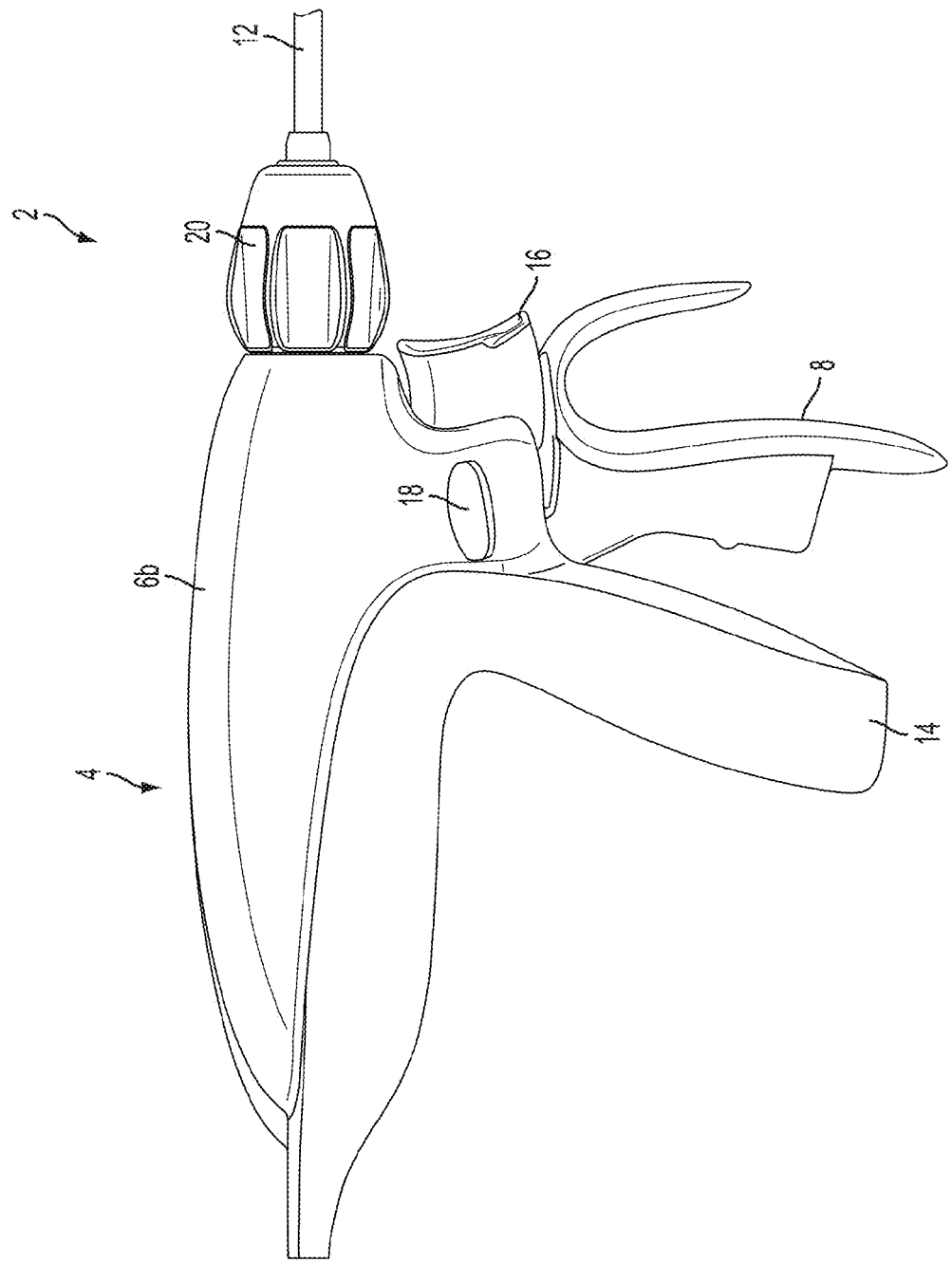
FIG. 3 illustrates a side-view of the electrosurgical instrument of FIG. 1.

FIG. 2 illustrates a side perspective view of the electrosurgical instrument 2 illustrated in FIG. 1. FIG. 2 illustrates the right handle housing 6b. The energy button 18 extends through the handle assembly 4 and is accessible on both sides of the handle assembly 4. The closure trigger 8, the firing trigger 14, and the energy button 18 comprise an ergonomic design. In some embodiments, the handle assembly 14 is thinner near the energy button 18 to allow ease of access to the energy button 18 by a clinician. In some embodiments, the energy button 18 is disposed on either the left handle housing 6a or the right handle housing 6b. FIG. 3 illustrates a side view of the electrosurgical instrument 2 and the right handle housing 6b.

Figure 4:
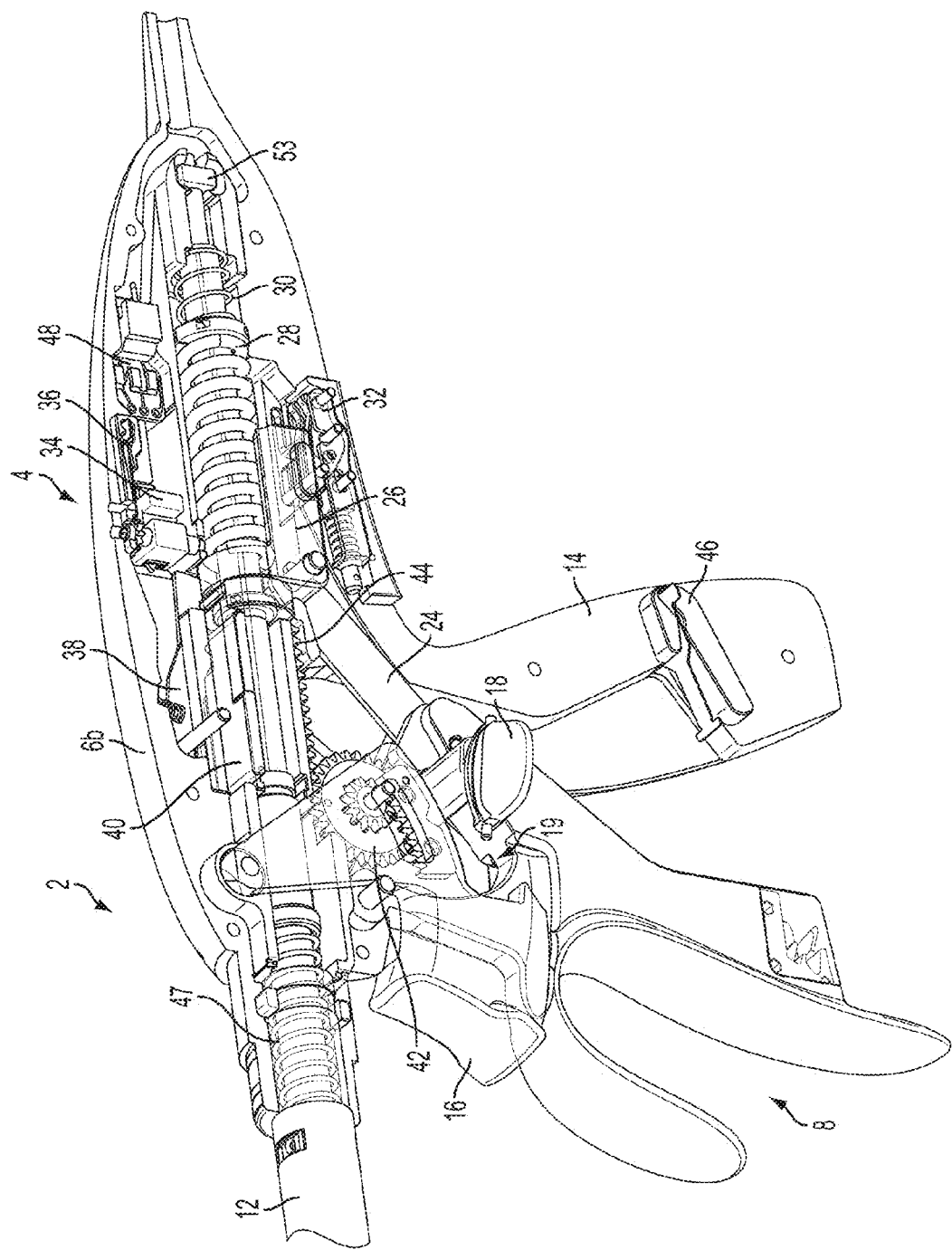
FIG. 4 illustrates a perspective view of the electrosurgical instrument of FIG. 1 with a left handle housing removed.

FIG. 4 illustrates one embodiment of the surgical instrument 2 of FIG. 1 with the left handle housing 6a removed. The handle assembly 4 comprises a plurality of components for actuating the surgical instrument 2, such as, for example, mechanisms for affecting closure of the jaws 22a, 22b of the end effector 10, deploying a cutting member within the end effector 10, and/or delivering energy to the electrode 92 coupled to the end effector 10. A closure trigger 8 is configured to transition the jaws 22a, 22b from an open position to a closed position. The closure trigger 8 is connected to a clamp arm 24. The clamp arm 24 couples the closure trigger 8 to a yoke 26. When the closure trigger 8 is actuated towards the pistol grip handle 14, the yoke 26 moves proximally and compresses a clamp spring 28. Compression of the clamp spring 28 retracts a jaw actuator, such as, for example, the outer sheath 23, to transition the first jaw member 22a of the end effector 10 from an open position to a closed position. In the illustrated embodiment, the clamp spring 28 comprises an uncompressed spring. In some embodiments, a partially pre-compressed spring may be used (see FIG. 25).

A firing trigger 16 is configured to deploy a cutting member within the end effector 10. The firing trigger 16 is operatively coupled to a compound gear 42. The compound gear 42 interfaces with a rack 44. The rack 44 is coupled to a firing actuator (not shown). When the firing trigger 16 is actuated, the compound gear 42 rotates and moves the rack 44 distally. The distal movement of the rack 44 causes distal movement of the firing actuator and deployment of the cutting member within the end effector 10. The cutting member is deployed from the proximal end of the end effector 10 to the distal end. In one embodiment, the firing trigger 16 comprises a high pivot to provide a linear feel during actuation of the firing trigger 16. The linear feel provides increased control and comfort to a clinician actuating the firing trigger 16.

In some embodiments, the rack 44 comprises a lock mechanism. In the illustrated embodiment, the rack 44 comprises a rack unlock block 40. The rack unlock block 40 interfaces with a lock arm 38 to prevent actuation of the cutting member firing switch 16 prior to actuation of the closure trigger 8. When the closure trigger 8 is in an open position, the lock arm 38 interfaces with the rack unlock block 40 to lock the rack 44 and prevent actuation of the firing trigger 16. When the closure trigger 8 is actuated, the yoke 26 raises the lock arm 38 away from the rack unlock block 40. When the closure trigger 8 is sufficiently actuated, corresponding to the jaws 22a, 22b of the end effector 10 being in a sufficiently closed position to prevent the cutting member from existing a slot in the jaws 22a, 22b, the lock arm 38 is decoupled from the rack unlock block 40, allowing actuation of the firing trigger 16.

Figure 5:
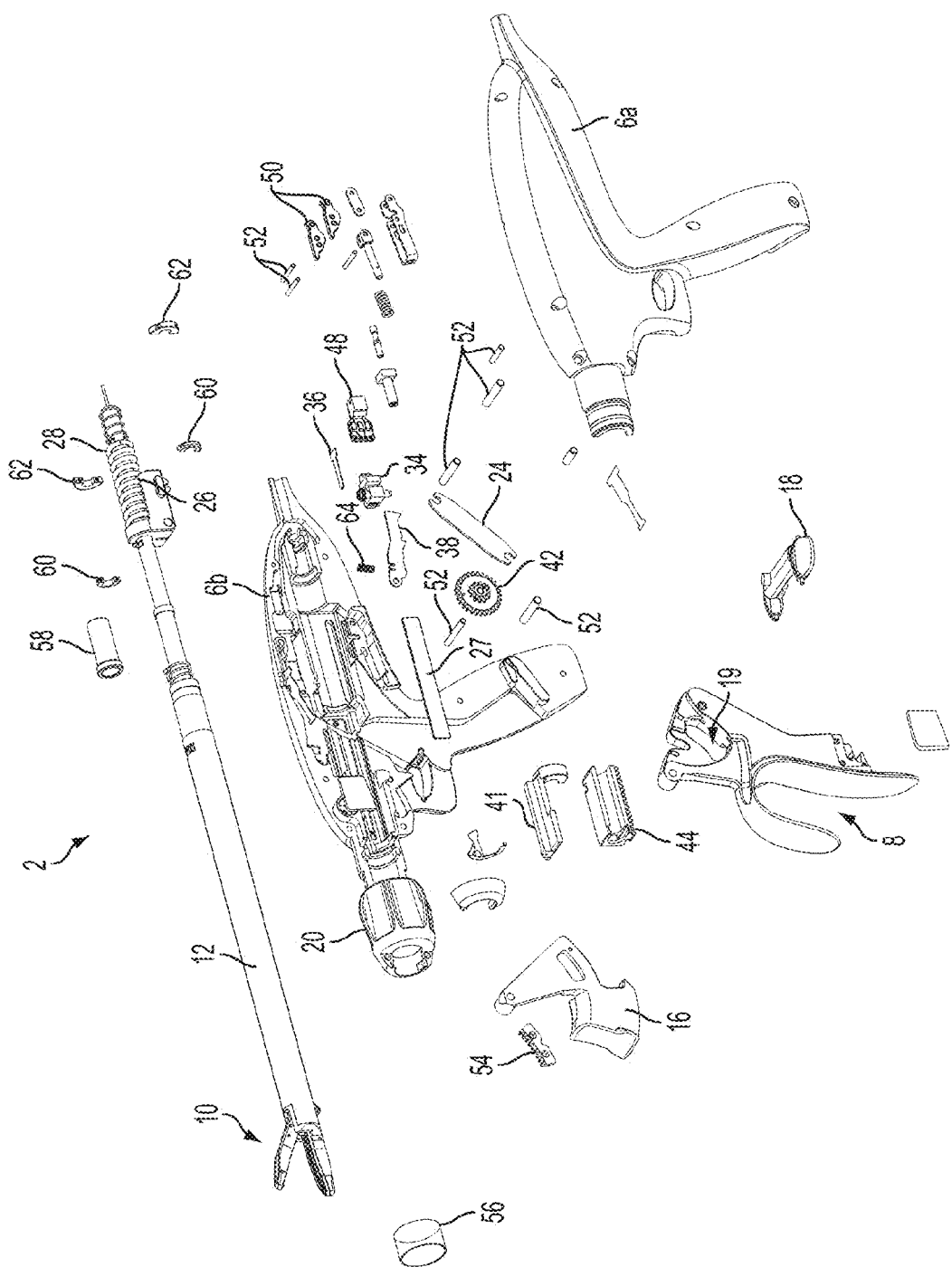
FIG. 5 illustrates an exploded view of the electrosurgical instrument of FIG. 1.

FIG. 5 illustrates an exploded view of the electrosurgical instrument 2. As shown in FIG. 5, the handle assembly 4 comprises a left handle housing 6a and a right handle housing 6b. The handle assembly 4 comprises a closure trigger 8, a firing trigger 16, and an energy button 18. A clamp arm 24 is coupled to the jaw closure trigger 8 and a yoke 26 by a plurality of pins 52. A mil max connector 53 is located at a proximal end of the handle assembly 4 to couple to an energy source (not shown). Although the illustrated embodiments comprise a surgical instrument 2 coupled to an external energy source, those skilled in the art will recognize that the energy source and/or one or more drive circuits may be located within the handle assembly 4. For example, in one embodiments, a battery and a RF generation circuit may be mounted in the handle assembly 4 and coupled to the energy button 18. In some embodiments, a jaw position sensor 34 is mounted in the handle assembly 4 to indicate when the jaws 22a, 22b of the end effector 10 have closed beyond a predetermined position. A screw lock spring 36 is mounted to the jaw position sensor 34 to prevent accidental adjustment of the jaw position sensor 34. A control board 48 is mounted in the handle assembly 4.

Figure 6:
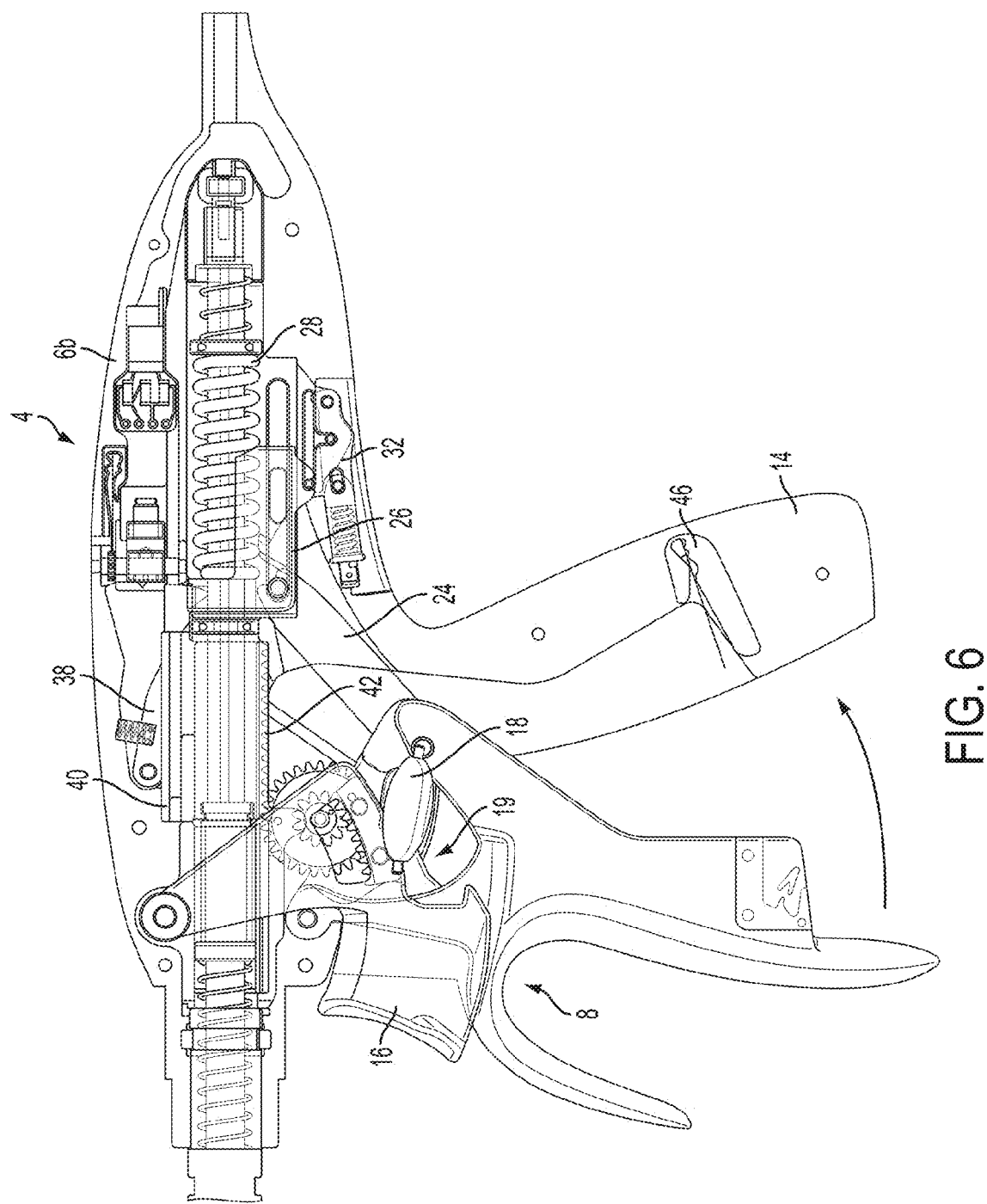
FIG. 6 illustrates a side view of the electrosurgical instrument FIG. 1 comprising a jaw closure system in the handle assembly.
Figure 7:
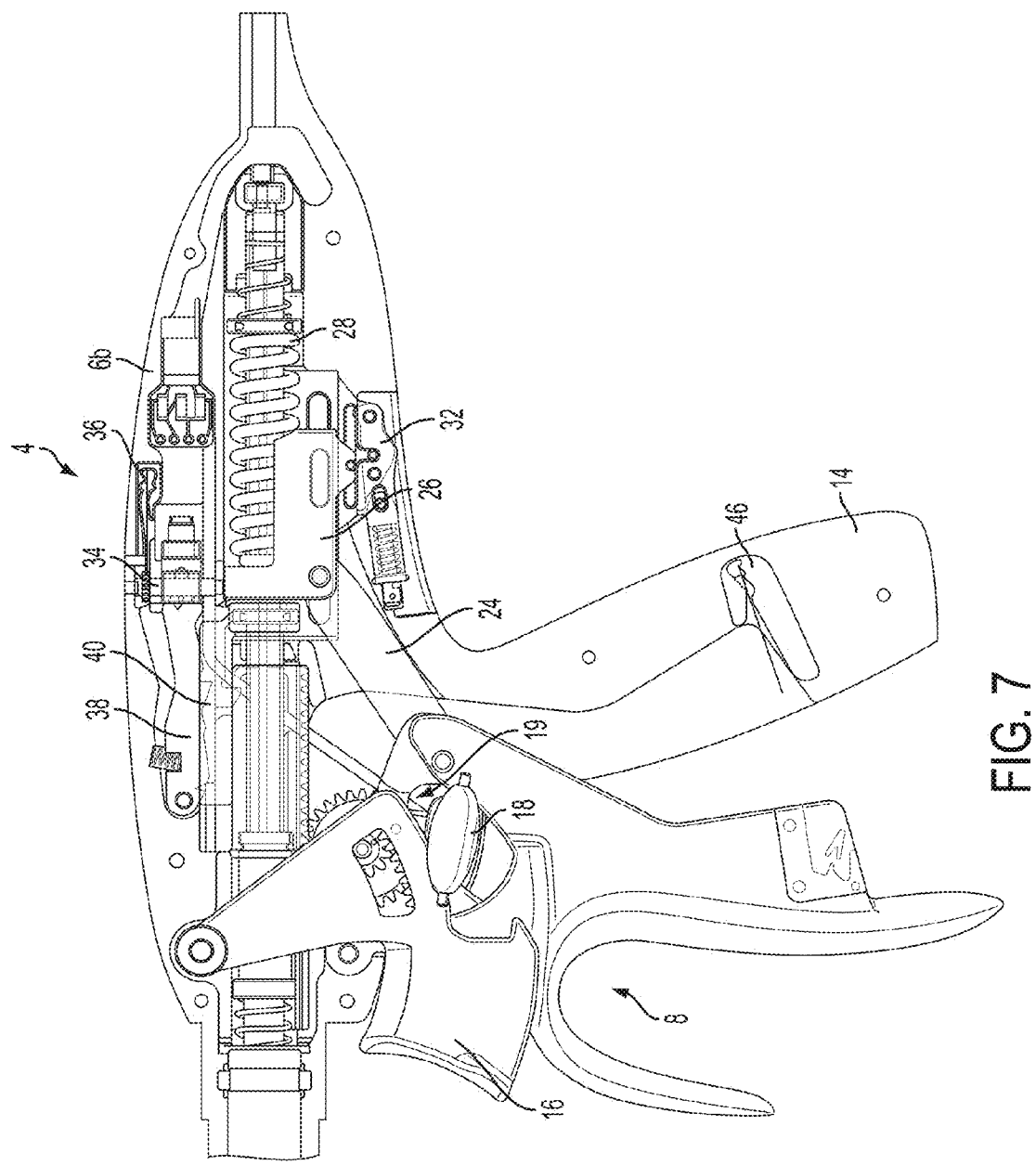
FIG. 7 illustrates the electrosurgical instrument of FIG. 6 with the jaw closure system in a partially-closed position.

FIG. 6 illustrates a side perspective of the handle assembly 4 comprising a jaw closure mechanism in the handle assembly 4. The closure trigger 8 is illustrated in an initial position corresponding to an open position of the jaws 22a, 22b. In operation, a clinician actuates the closure trigger 8 to transition the jaws 22a, 22b to a closed position. FIG. 7 illustrates the closure trigger 8 in a partially actuated position. As shown in FIG. 7, as the closure trigger 8 is rotated proximally towards the pistol-grip handle 14, the clamp arm 24 moves the yoke 26 in a proximal direction to compress the clamp spring 28. Compression of the clamp spring 28 causes the jaws 22a, 22b to transition to a closed position and applies a force to tissue grasped between the jaws 22a, 22b. For example, in some embodiments, the closure trigger 8 position illustrated in FIG. 7 corresponds to a full closure of the jaws 22a, 22b.

Additional actuation of the closure trigger 8 increases the force applied by the jaws 22a, 22b to a tissue section grasped therebetween. In other embodiments, full closure of the jaws 22a, 22b occurs when the closure trigger 8 is fully actuated. A hole 19 in the closure trigger 8 allows the closure trigger 8 to be actuated without interfering with the energy button 18. In some embodiments, the hole 19 is covered by the left and right handle housings 6a, 6b.

Figure 8:
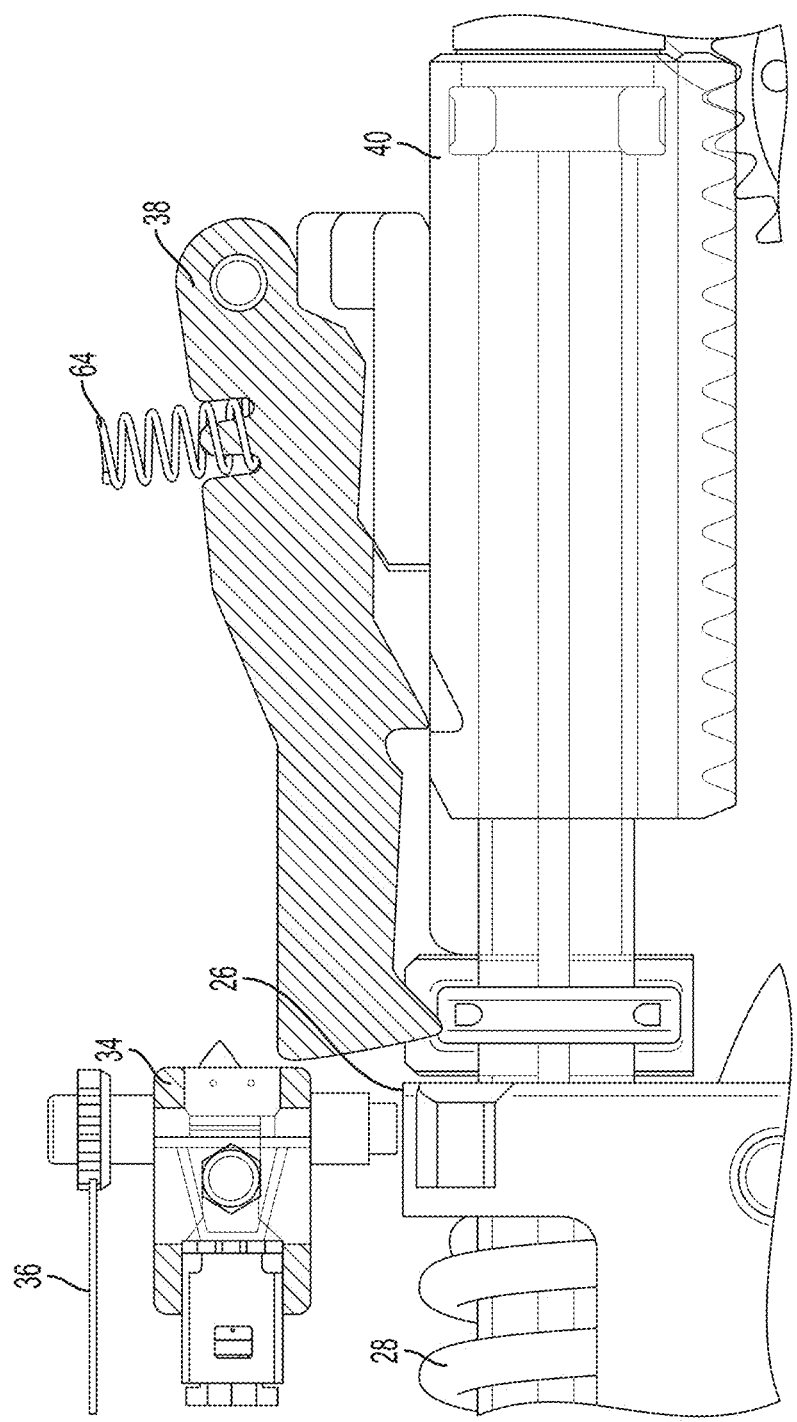
FIG. 8 illustrates a firing mechanism lock-bar interfaced with cutting member firing mechanism.
Figure 9:
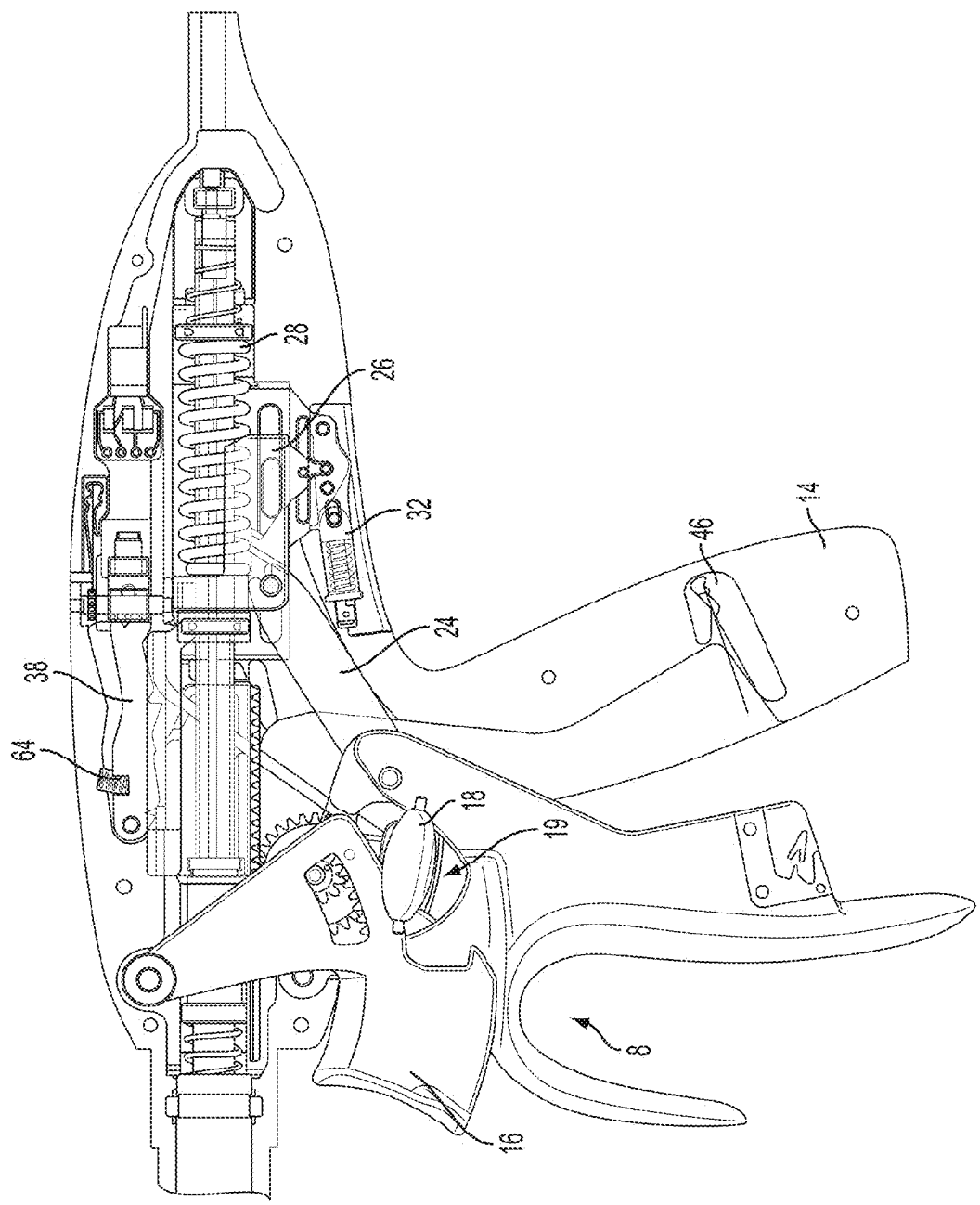
FIG. 9 illustrates a closure trigger rotated sufficiently to disengage a lock bar from a rack unlock block.
Figure 10:
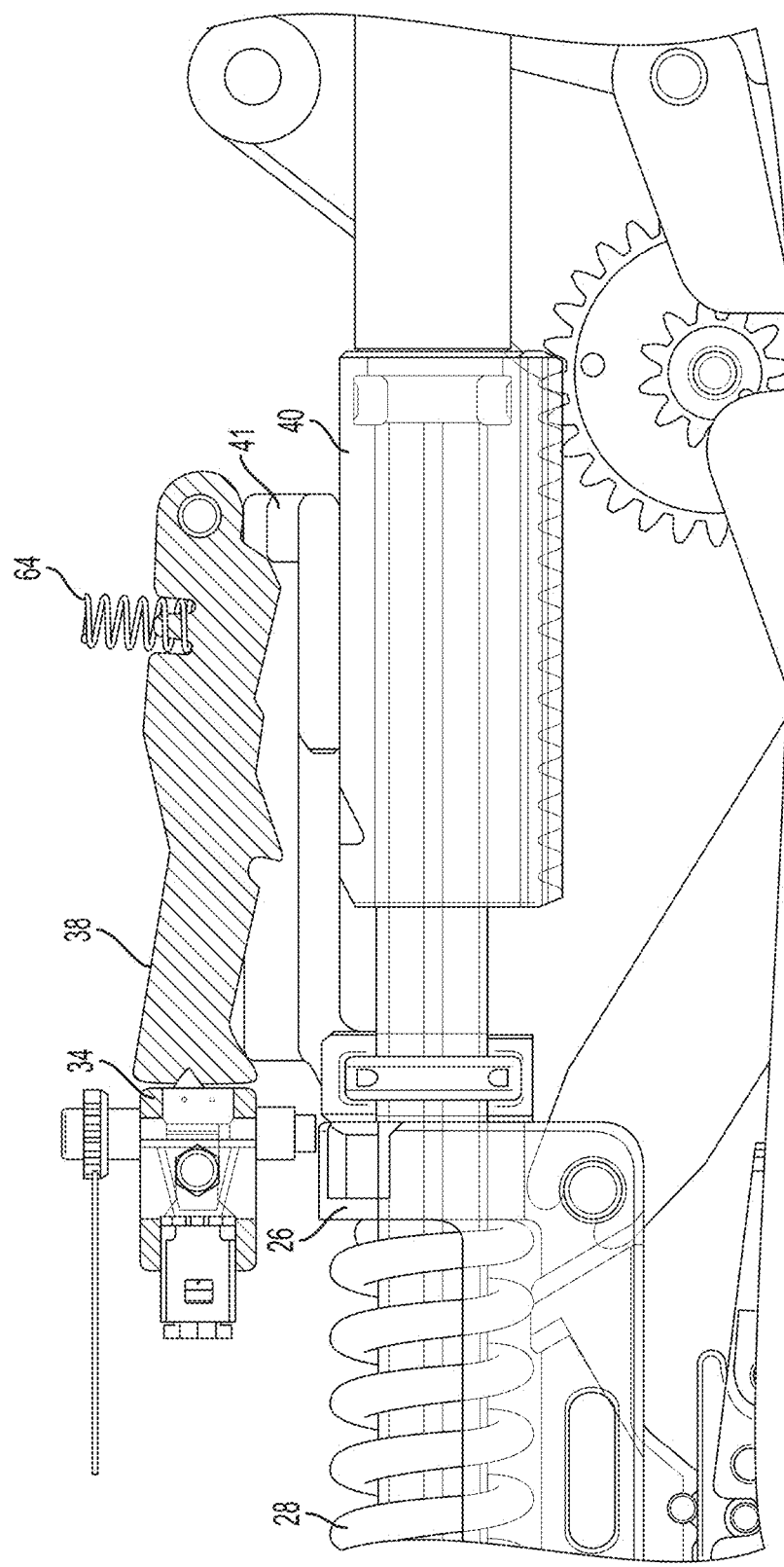
FIG. 10 illustrates the firing mechanism lock-bar of FIG. 8 in an unlocked position.

FIG. 8 illustrates a firing trigger lock mechanism 33. A lock arm 38 interfaces with a rack unlock block 40 to prevent actuation of the firing trigger 16 prior to closure of the jaws 22a, 22b. The firing trigger lock mechanism 33 is unlocked through actuation of the closure trigger 8. The yoke 26 is coupled to an unlock bar 41. When the yoke 26 is moved distally through actuation of the closure trigger 8, the lock bar 41 lifts the lock arm 38 vertically away from the rack unlock block 40. When the lock arm 38 has been lifted a sufficient distance, the rack 44 is allowed to move distally and the firing trigger 16 is actuatable to deploy the cutting member within the end effector 10. FIGS. 9 and 10 illustrate the handle assembly 4 of the surgical instrument 2 with the jaw clamping trigger 8 sufficiently compressed to release the lock arm 38 from the rack unlock block 40. As can be seen in FIG. 9, the lock arm 38 is lifted a sufficient distance to allow actuation of the firing trigger 16 prior to full rotation of the closure trigger 8. The firing trigger 16 is unlocked when the jaws 22a, 22b are sufficiently closed such that the cutting member cannot skip out of a slot formed in the end effector 10. For example, in some embodiments, the lock arm 38 is released when the closure trigger 8 is compressed about 8 degrees, corresponding to jaw opening of about 2.5 degrees. In other embodiments, the lock arm 38 may be released at a lower or higher degree of rotation of the closure trigger 8.

In some embodiments, a lock spring 64 is coupled to the lock arm 38 to apply a biasing force to the lock arm 38. The biasing force biases the lock arm 38 towards the rack unlock block 40 and maintains the lock arm 38 in contact with the rack unlock block 40 until the closure trigger 8 has been sufficiently actuated. When the closure trigger 8 is released and the yoke 26 returns to a rest position, the lock spring 64 biases the lock arm 38 back into a locked configuration with the rack unlock block 40.

FIG. 10 illustrates the lock arm 38 in an unlocked position. In the unlocked position, a clinician may actuate the firing trigger 16 to drive the rack 44 distally and deploy the cutting member within the end effector 10. In some embodiments, a jaw position sensor 34 is configured to indicate when the jaws 22a, 22b are sufficiently closed to allow deployment of the cutting member. In some embodiments, the jaw position sensor 34 comprises a bypass switch. In other embodiments, other types of switches may be used, such as, for example, normally open, normally closed, and/or other switch types.

Figure 11:
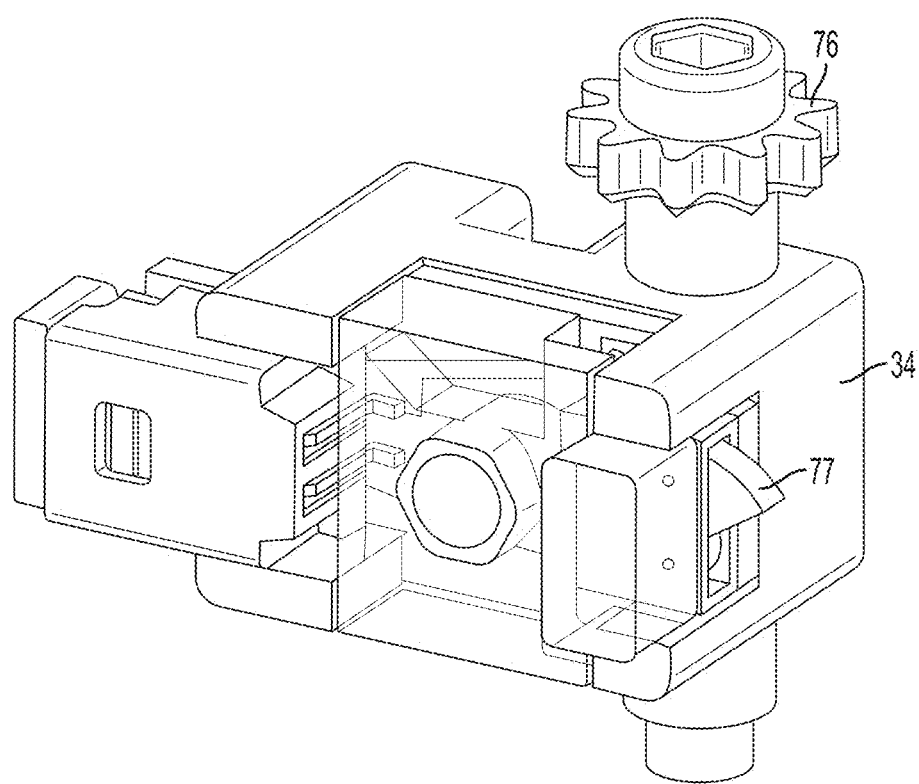
FIG. 11 illustrates one embodiment of a jaw position sensor.
Figure 12:
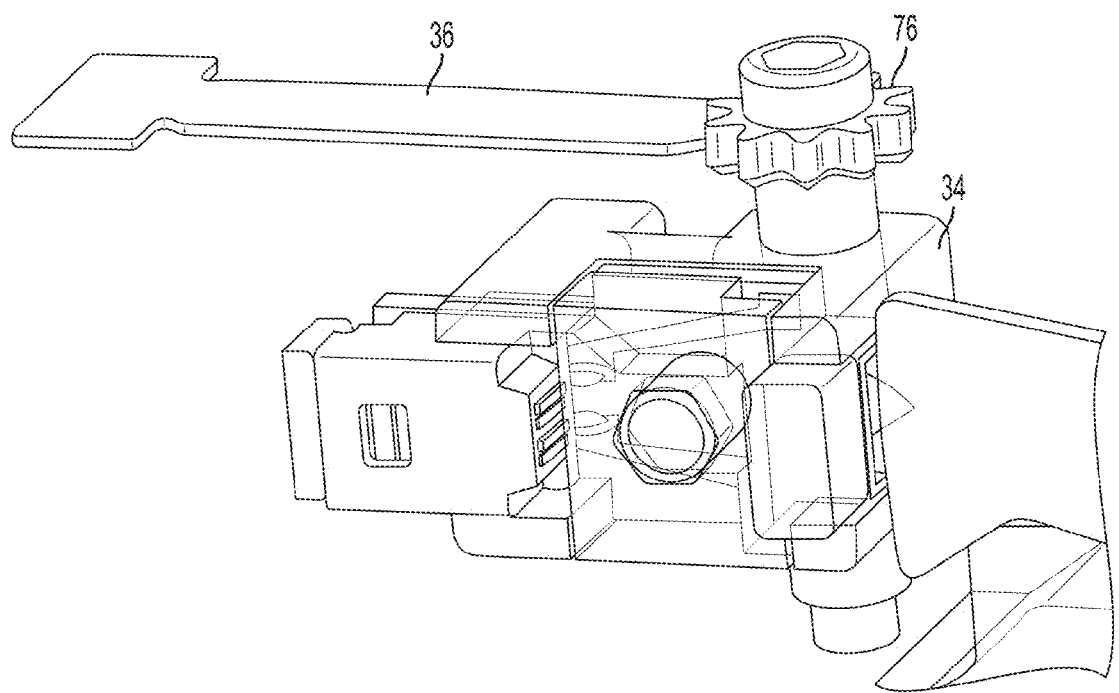
FIG. 12 illustrates one embodiment of a jaw position sensor comprising an adjustment screw lock spring.

FIG. 11 illustrates one embodiment of a jaw position sensor 34. The jaw position sensor 34 comprises an adjustable contact 77. The adjustable contact 77 is mechanically adjustable to adjust the jaw sense activation point of the jaw position sensor 34. The contact 77 is adjusted by rotating a screw 76 coupled to the jaw position sensor 34. Rotation of the screw 76 increases or decreases (depending on the direction of rotation) the necessary height of the lock arm 38, corresponding to a specific rotation of the closure trigger 8, required to activate the jaw position sensor 34. In some embodiments, such as the embodiment illustrated in FIG. 12, a screw lock spring 36 is coupled to the screw 76 to prevent accidental adjustment of the contact 77. In order to adjust the contact 77 in the embodiment illustrated in FIG. 12, the screw lock spring 36 must be depressed prior to rotation of the screw 76.

The screw lock spring 36 is released after adjustment of the screw 76 to lock the screw 76 in place. In some embodiments, the screw 76 comprises a locking thread. Activation of the jaw position sensor 34 may correspond to, for example, a distance of about 0.01 inches between the first jaw 22a and the second jaw 22b.

Figure 13:
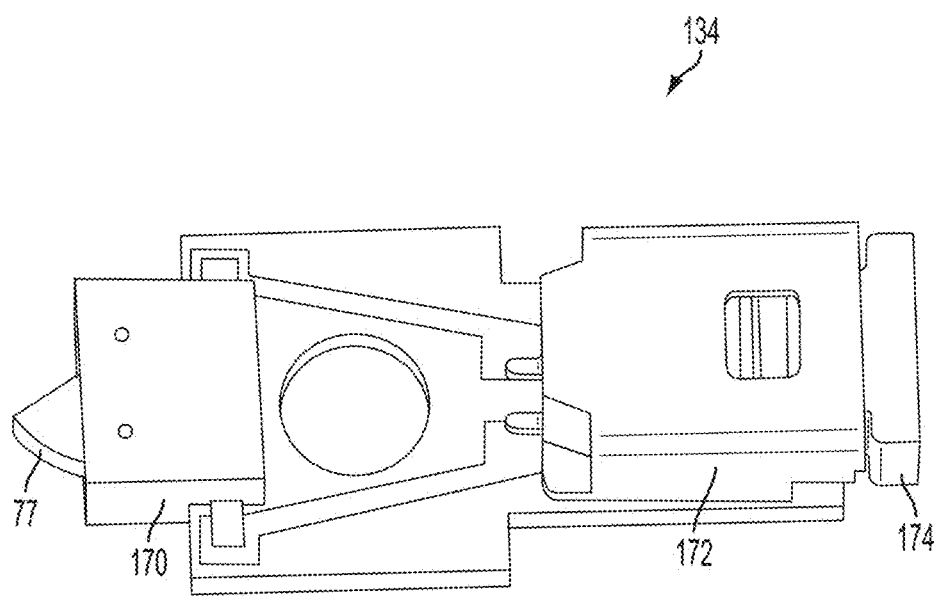
FIG. 13 illustrates one embodiment of a jaw position sensor.
Figure 14:
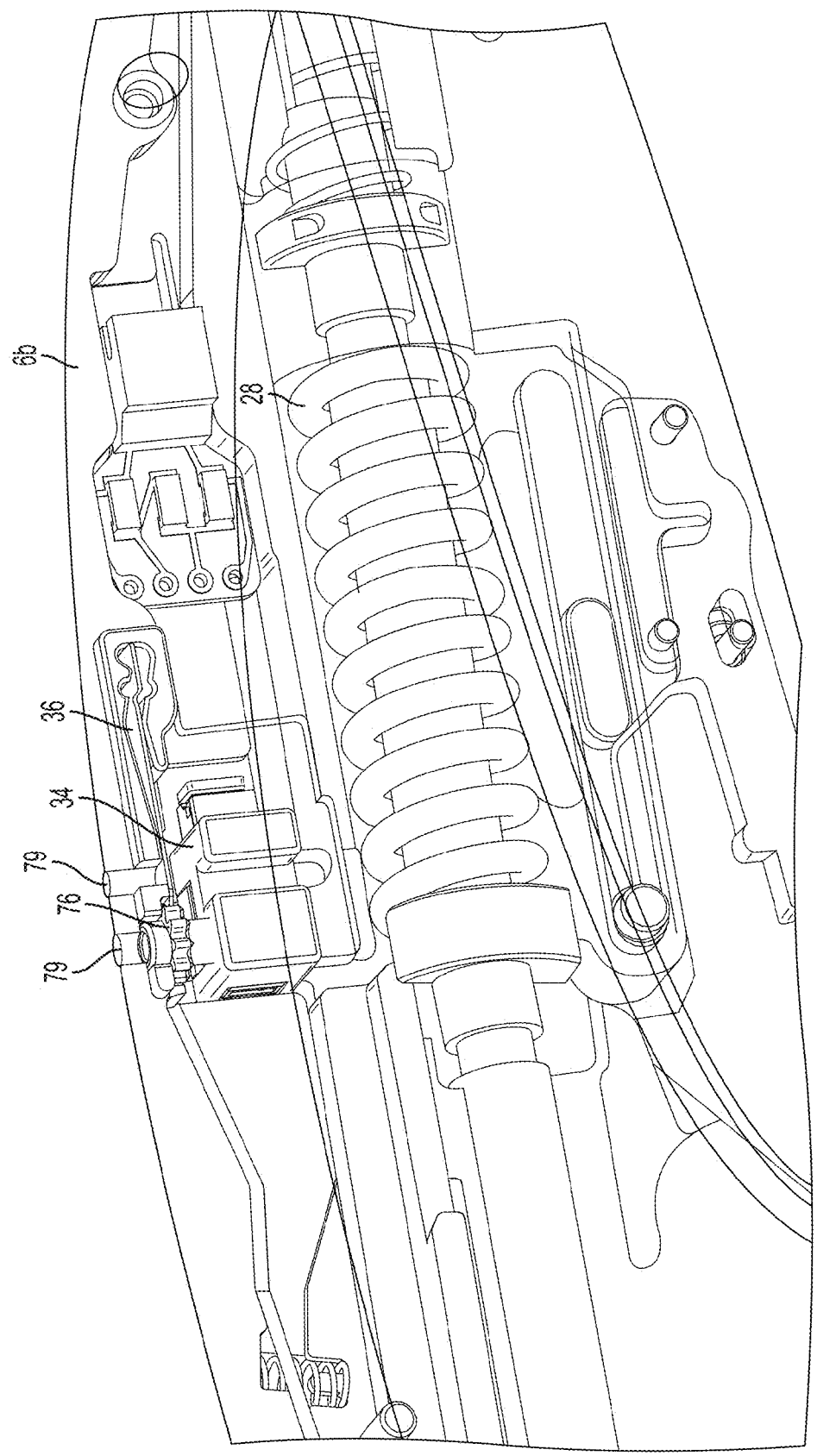
FIG. 14 illustrates one embodiment of a jaw position sensor mounted in a handle assembly.

FIG. 13 illustrates one embodiment of a jaw position sensor 134. The jaw position sensor 134 comprises a switch 170. When the contact 177 of the switch 170 is depressed by the lock bar 41, an electrical connection within the switch 170 is opened. The break in the electrical connection of the switch 170 is detected by a two-position connection header 172. The connection header 172 is coupled to, for example, a control board 38. A connected receptacle 174 couples the connection header 172 to the handle assembly 4. FIG. 14 illustrates the jaw sensor 34 mounted in the handle assembly 4. The handle assembly 4 comprises a plurality of access holes 79 to allow a clinician to depress the screw lock spring 36 and to rotate the screw 76 to adjust the contact 77.

Figure 15:
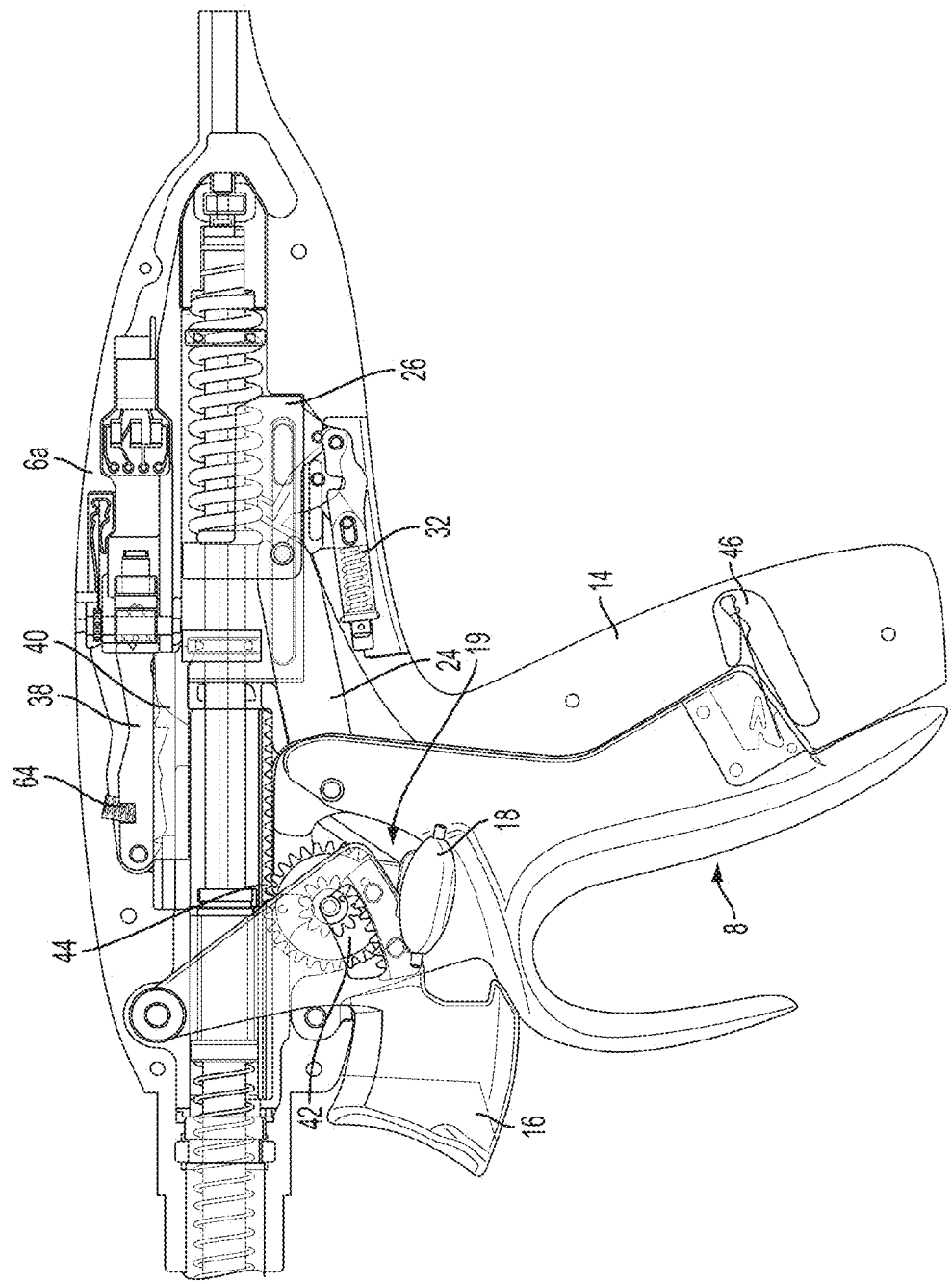
FIG. 15 illustrates one embodiment of the electrosurgical instrument of FIG. 4 with the closure trigger fully actuated.

FIG. 15 illustrates one embodiment of the handle assembly 4 with the closure trigger 8 fully actuated. When the closure trigger 8 is fully actuated, the yoke 26 compresses the clamp spring 28 to a maximum compression, corresponding to a maximum force applied by the jaws 22a, 22b. In some embodiments, the jaws 22a, 22b may be configured to maintain a minimal spacing therebetween to prevent damage to components of the surgical instrument 2 and/or the tissue section. In other embodiments, the maximum compression of the clamp spring 28 corresponds to a fully closed position of the jaws 22a, 22b. In some embodiments, full actuation of the closure trigger 8 corresponds to a rotation of about 30 degrees. When the closure trigger 8 is fully rotated against the pistol-grip handle 14, a closure trigger lock 46 is engaged to maintain the closure trigger 8 in a rotated position and therefore maintain the jaws 22a, 22b in a closed position. As shown in FIG. 15, the hole 19 in the closure trigger 8 allows the closure trigger 8 to be fully rotated against the pistol-grip handle 14 without interfering with the energy button 18. Once the trigger lock 46 has been engaged, the clinician may release the closure trigger 8 and the trigger lock 46 maintains the closure trigger 8 in a closed position, as illustrated in FIG. 16.

Figure 16:
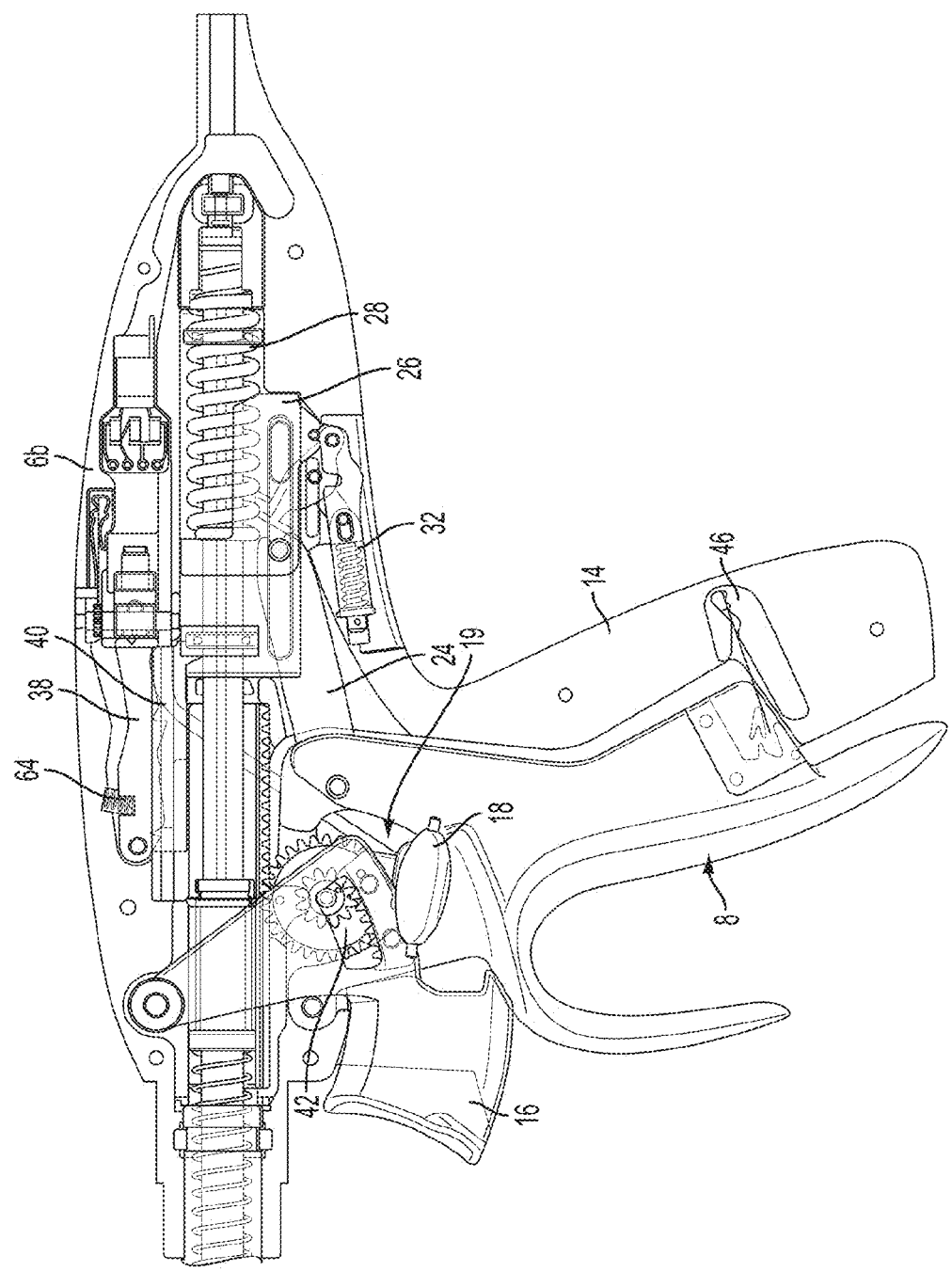
FIG. 16 illustrates the electrosurgical instrument of FIG. 4 with a closure trigger lock engaged.

As shown in FIG. 16, the trigger lock 46 maintains the closure trigger 8 in a less than fully retracted position to prevent damage to components of the surgical instrument 2 due to over application of force to the jaws 22a, 22b. The trigger lock 46 maintains the closure trigger 8 in a sufficiently rotated position to release the lock arm 38 from the rack unlock block 40 and to engage the jaw position sensor 34. For example, in the illustrated embodiment, the trigger lock 46 maintains the closure trigger 8 at a rotation of about 28 degrees. With the closure trigger 8 in a locked position, the clinician may actuate the firing trigger 16 to deploy the cutting member within the end effector 10. In some embodiments, the clinician may actuate the energy button 18 to deliver energy to a tissue section grasped between the jaws 22a, 22b prior to or simultaneously with, deployment of the cutting member.

Figure 32:
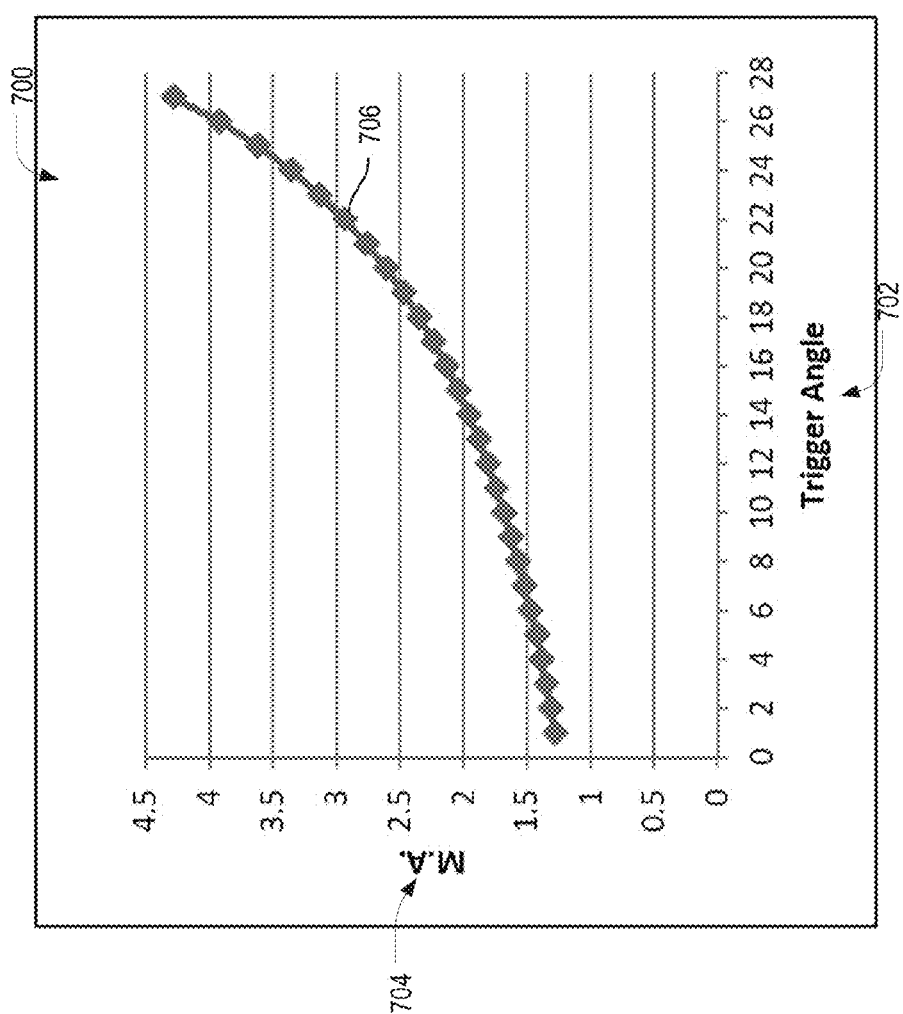
FIG. 32 shows a graph illustrating the mechanical advantage of the closure trigger at various trigger angles.
Figure 33:
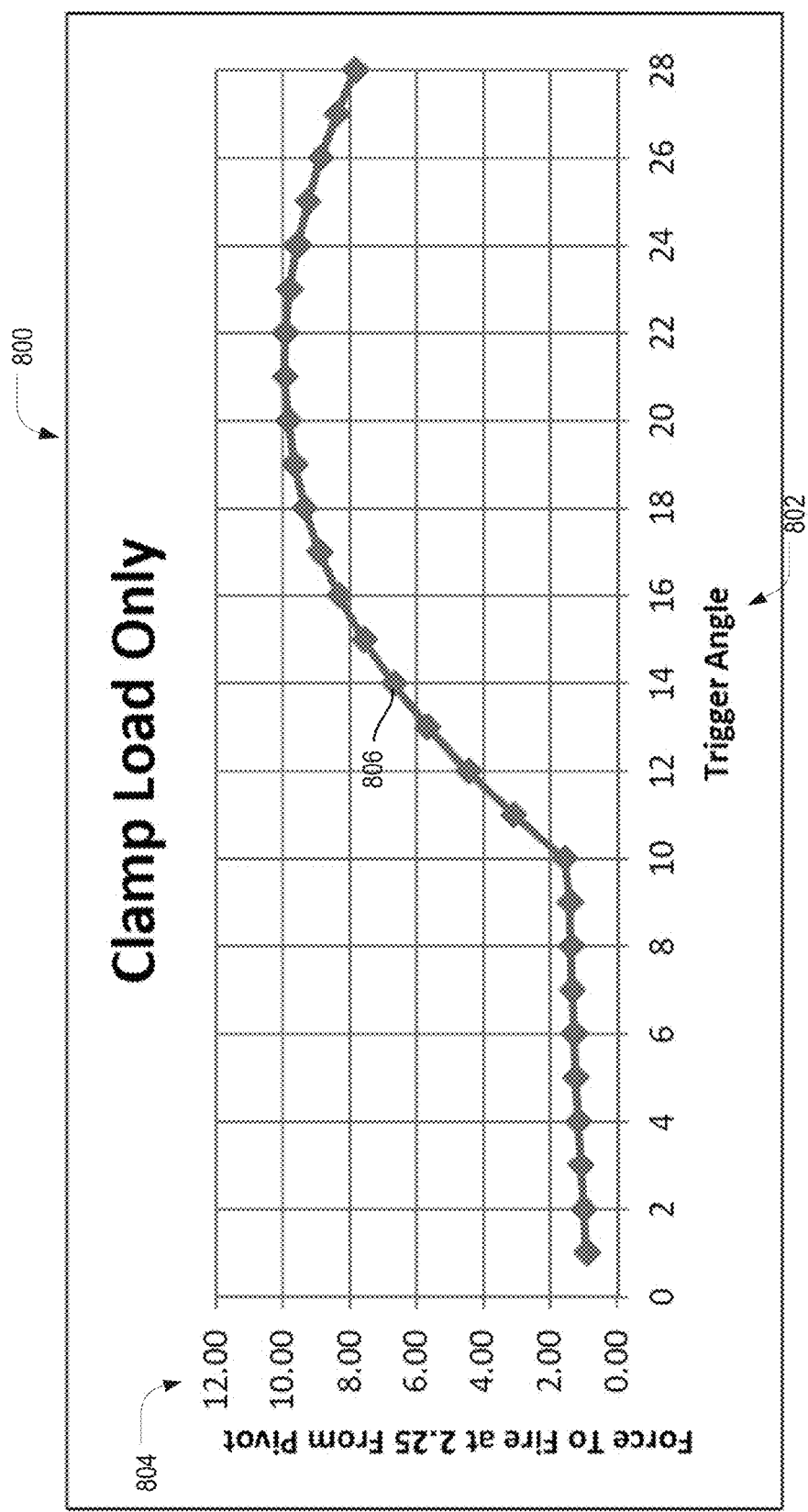
FIG. 33 shows a graph illustrating force delivered by the jaws when no tissue is located within the jaws.
Figure 34:
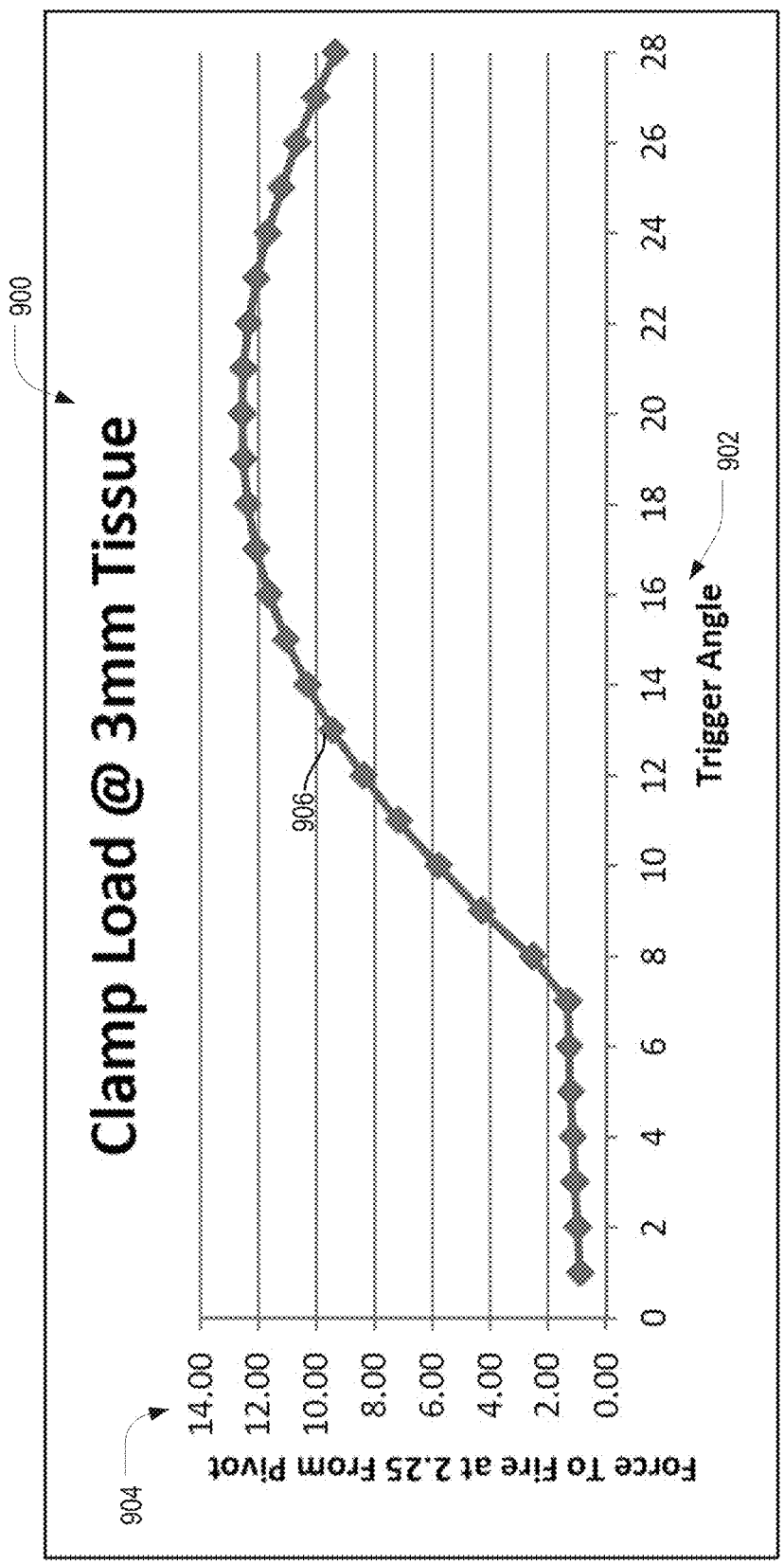
FIG. 34 shows a graph illustrating force delivered by the jaws when a tissue section is located within the jaws.

In various embodiments, the closure trigger 8 provides a mechanical advantage in transferring force from the closure trigger 8 to the jaws 22a, 22b. FIG. 32 is a chart 700 illustrating the mechanical advantage 704 of the closure trigger 8 at various trigger angles 702. As shown in FIG. 32, as the angle of the closure trigger 8 increases, for example, by actuating the closure trigger 8 towards the pistol-grip handle 14, the mechanical advantage 704 delivered by the clamp spring 28 to the jaws 22a, 22b increases. FIGS. 33 and 34 illustrate the force provided by the jaws 22a, 22b as the closure trigger 8 is rotated towards the pistol-grip handle 14. FIG. 33 illustrates force 806 delivered by the jaws 22a, 22b when no tissue is located within the jaws 22a, 22b. FIG. 34 illustrates the force 906 delivered by the jaws 22a, 22b when a tissue of about 3 mm thickness is located between the jaws 22a, 22b.

Figure 17:
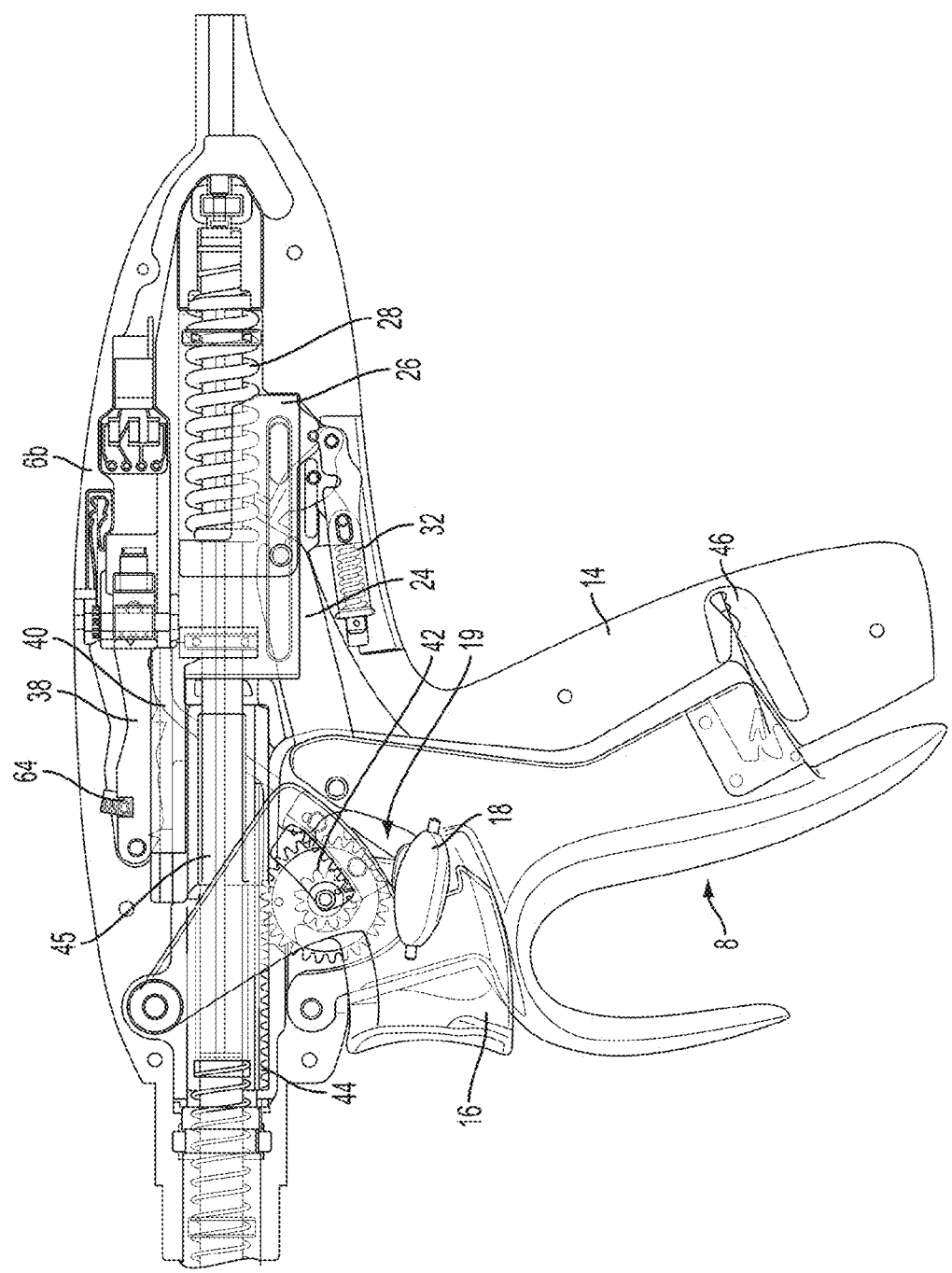
FIG. 17 illustrates the electrosurgical instrument of FIG. 16 with a firing trigger in an actuated position.

As illustrated in FIG. 16, the firing trigger 16 is coupled to a compound gear 42 interfaced with a rack 44. The rack 44 is mechanically coupled to a firing actuator (not shown) configured to deploy the cutting member distally within the end effector 10. Rotation of the firing trigger 16 proximally towards the handle assembly 4 causes the rack 44 to advance distally within the handle assembly 4 and drive the cutting member within the end effector 10. FIG. 17 illustrates the handle assembly 4 with the firing trigger 16 in an actuated position. The compound gear 42 has advanced the rack 44 distally, corresponding to the cutting member being located at a distal most position within the end effector 10. Advancement of the rack 44 in a distal direction compresses a spring washer 58. When the clinician releases the firing trigger 16, the spring washer forces the rack 44 in a proximal direction, withdrawing the cutting member from the end effector 10. The firing trigger 16 comprises a mechanical advantage that adjusts the force applied by the cutting member with respect to the force applied to the firing trigger 16. For example, in one embodiment, the firing trigger 16 comprises a mechanical advantage of 0.6, such that one pound of force applied to the firing trigger 16 corresponds to 0.6 pounds of force applied by the cutting member to a tissue section grasped within the end effector 10. In some embodiments, the firing trigger 16 comprises a maximum rotation corresponding to the cutting member being located at a distal-most portion of the end effector 10. For example, the firing trigger 16 may rotate about nineteen degrees to fully deploy the cutting member within the end effector 10. In some embodiments, the handle assembly 4 comprises a rack-biasing spring 47 configured to bias the rack in an proximal position. The closure trigger lock 46 is released to open the jaws 22a, 22b and release tissue grasped therein.

Figure 18:
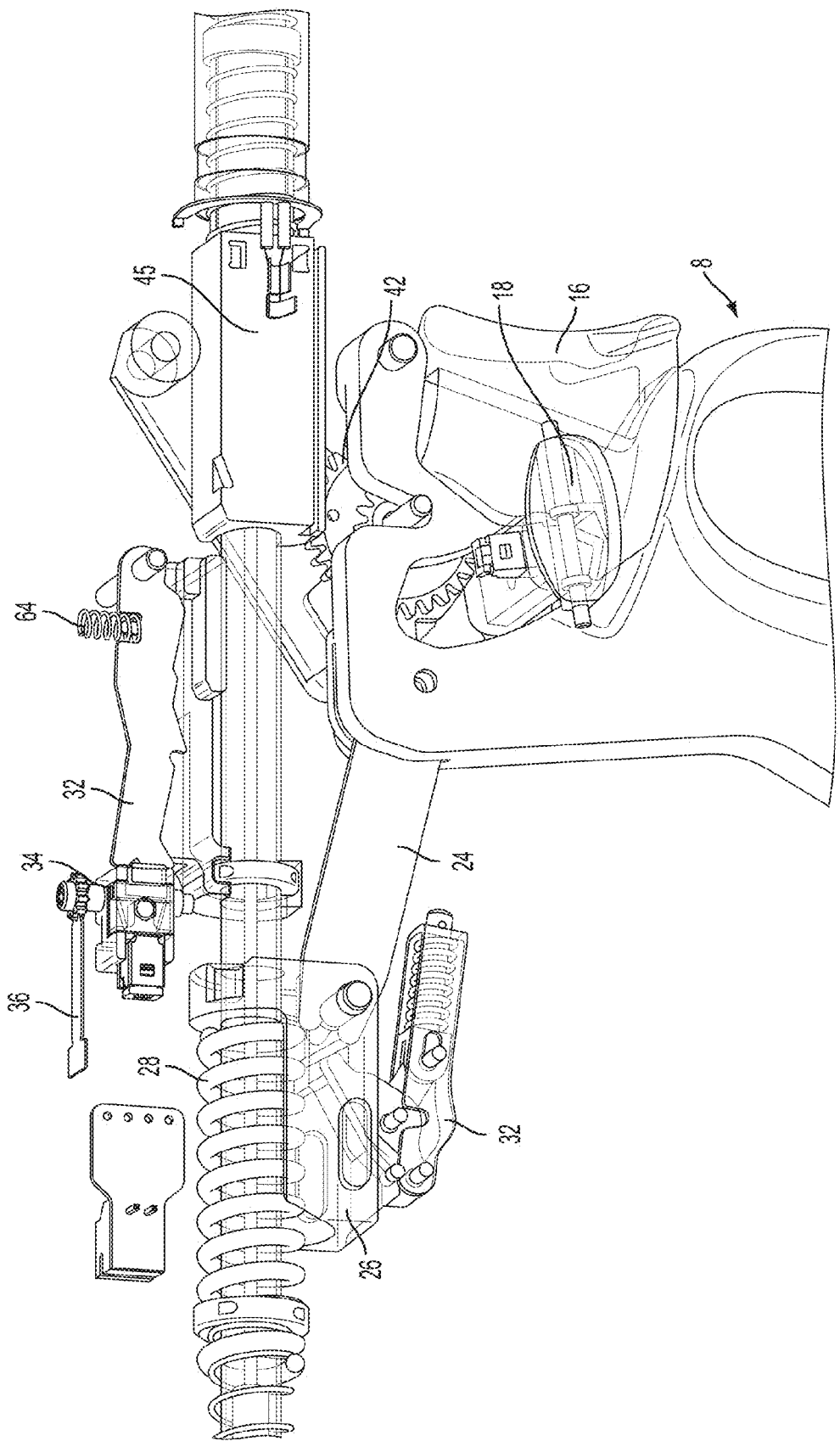
FIG. 18 illustrates one embodiment of a yoke of a jaw closure system coupled to a return stroke dampener.
Figure 19:
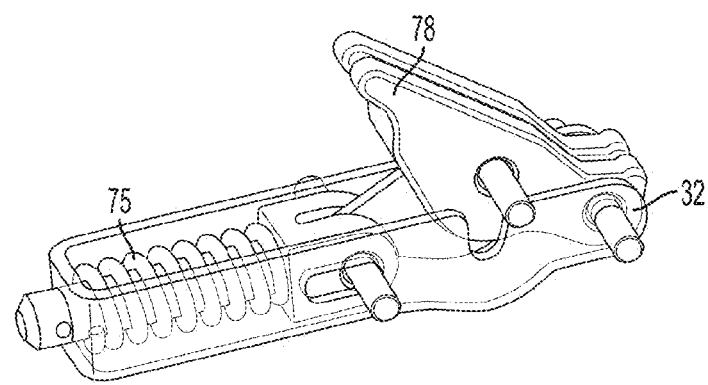
FIG. 19 illustrates one embodiment of return stroke dampener.
Figure 20A:
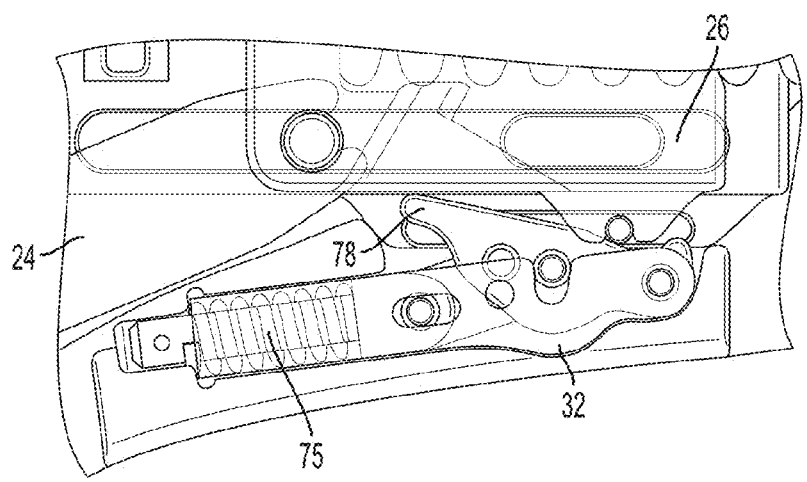
FIG. 20A illustrates the interface between a yoke and a return stroke dampener when the jaws of an end effector are in a closed position.
Figure 20B:
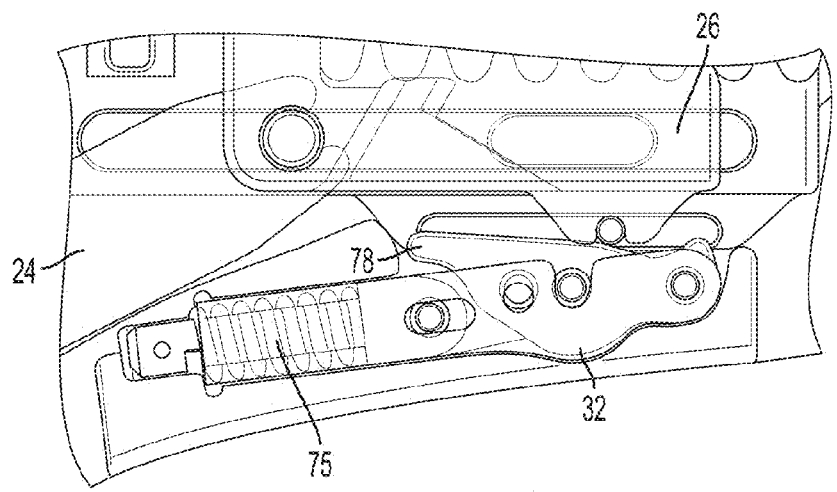
FIG. 20B illustrates the interface between the yoke and the return stroke dampener when the jaws of the end effector transition to an open position.

FIG. 18 illustrates one embodiment of a return stroke dampener 32 coupled to the yoke 26 to reduce the force of the return stroke of the clamp spring 28. The return stroke dampener 32 dampens the return stroke of the yoke 26 when the closure trigger 8 is released. FIG. 19 illustrates one embodiment of a return stroke dampener 32. FIGS. 20A and 20B illustrate an interface between the yoke 26 and the return stroke dampener 32. The return stroke dampener 32 comprises a toggle arm 78 and a dampening spring 76. The yoke 26 comprises a dampener interface pin 79. When the yoke 26 moves distally, for example, when the jaws 22a, 22b are released and the closure trigger 8 returns to an unactuated position, the interface pin 79 forces the toggle arm 78 down, compressing the dampening spring 76 and reducing the load from the closure spring 28 on the closure trigger 8. Once the interface pin 79 pushes the toggle arm 78 close to over center, the load on the yoke pin 79 goes almost to zero such that the dampener effect is eliminated for the remainder of the stroke. The return stroke dampener 32 reduces the force of the closure spring 28 when the closure trigger 8 is released from an actuated position.

Figure 35:
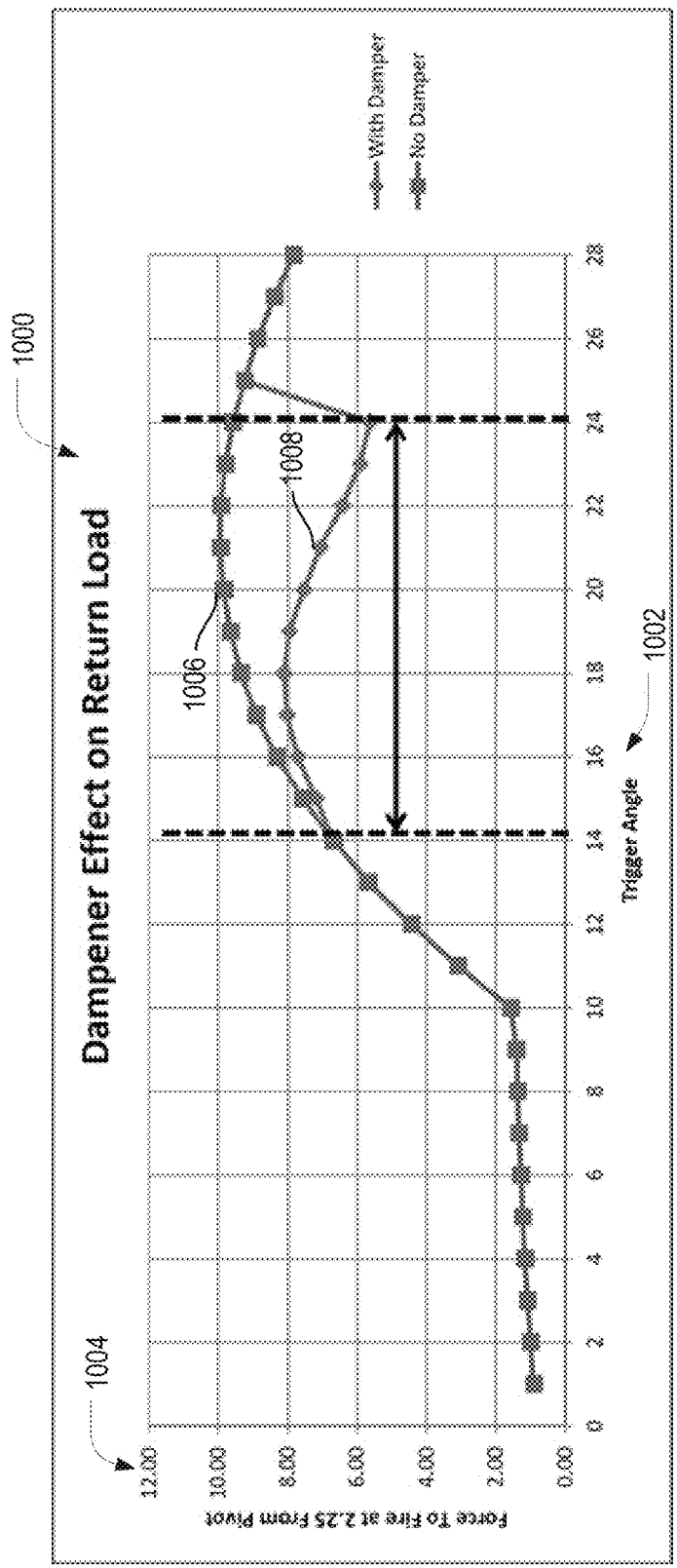
FIG. 35 shows a graph illustrating the dampener effect on a return load provided by a return stroke dampener.

FIG. 35 is a chart illustrating the dampener effect on a return load provided by a return stroke dampener 32. The chart 1000 illustrates the trigger angle 1002 of the closure trigger 8 plotted against the force 1004 applied to the closure trigger 8. As can be seen in FIG. 35, the force applied by the jaws 22a, 22b increases to a maximum point at about 18 degrees of rotation of the clamp trigger 8. The dampening force decreases as the clamp trigger 8 is released and the dampener toggle 78 crosses over a center point.

Figure 21:
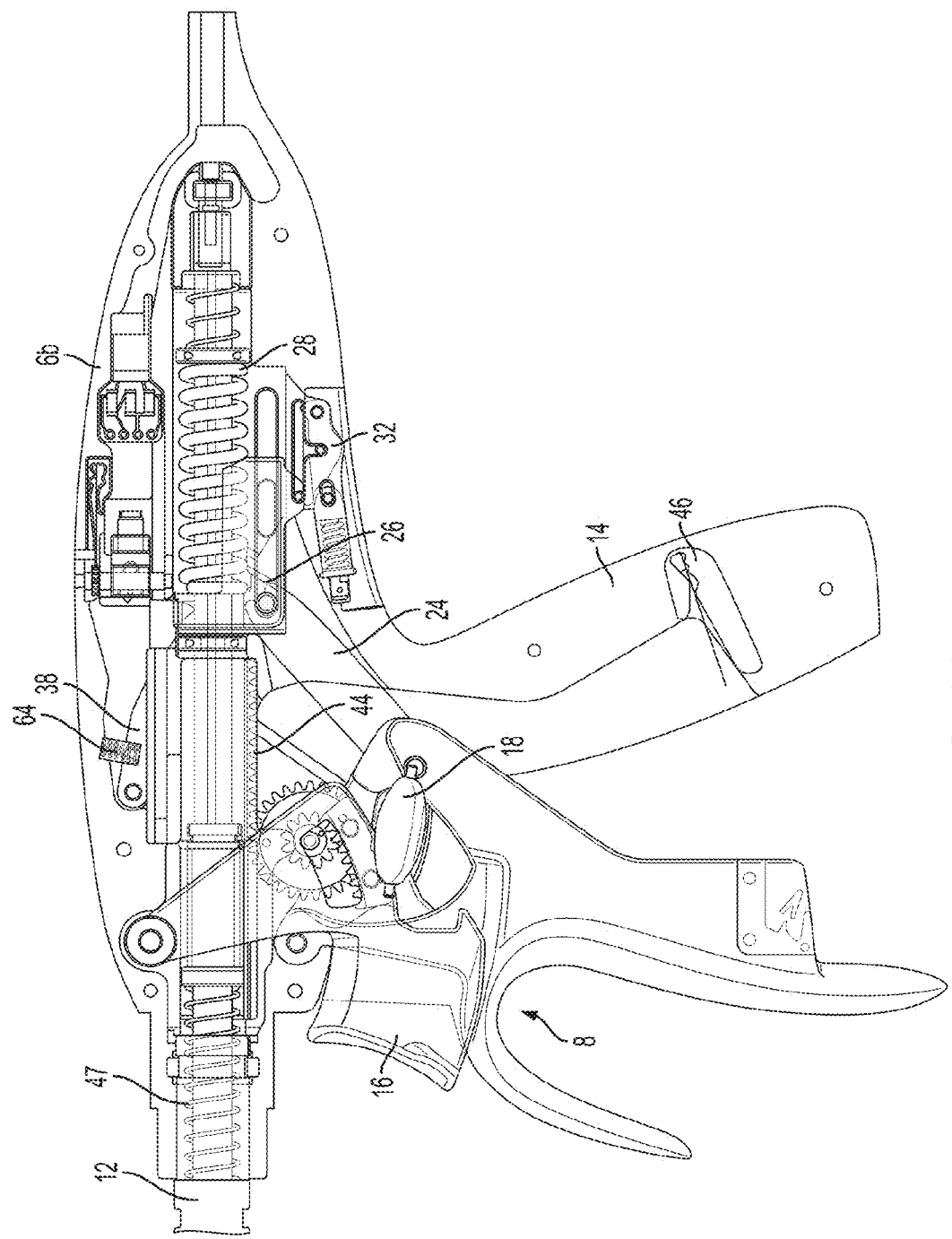
FIG. 21 illustrates the electrosurgical instrument of FIG. 4 with the closure trigger lock released and the closure trigger in a released position.
Figure 22:
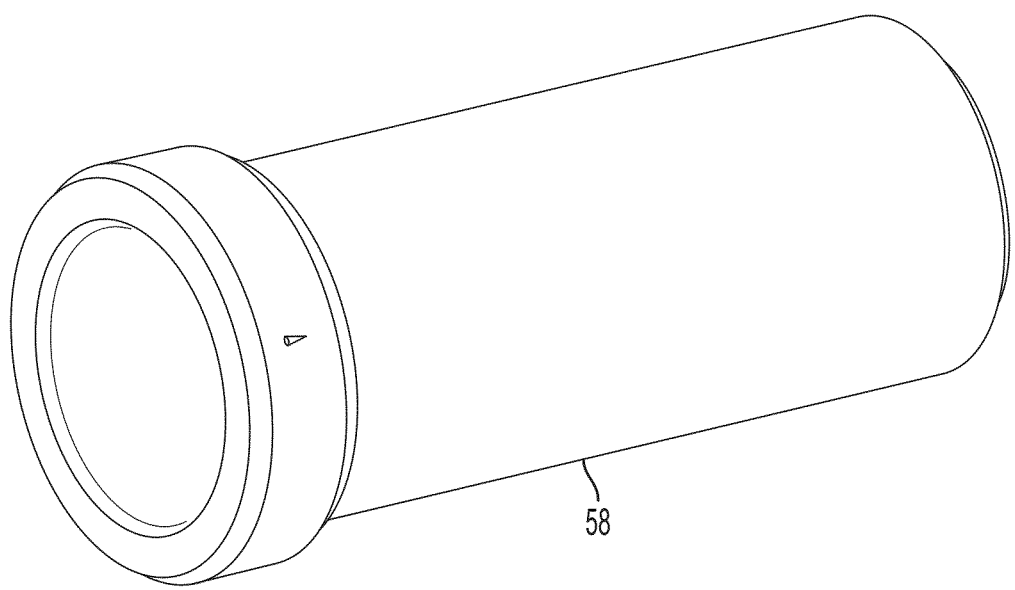
FIG. 22 illustrates one embodiment of a rack spring washer.
Figure 23:
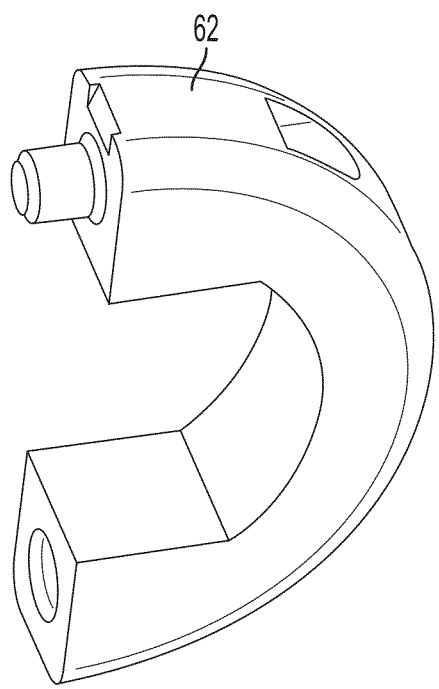
FIG. 23 illustrates one embodiment of a jaw closure spring stop.

FIG. 21 illustrates the handle assembly 4 after the closure trigger 8 has been released and the jaws 22a, 22b have assumed an open position. The closure trigger 8 has returned to an unactuated position with respect to the pistol-grip handle 14. The clamp spring 28 and the rack 44 have returned to their respective starting positions. The return stroke dampener 32 is fully compressed when the clamp spring 28 is in a rest position. FIG. 22 illustrates one embodiment of a spring washer 158 configured to interface with a rack spring 59 when the rack 44 is advanced in a distal direction. The spring washer 158 and the rack spring 59 cause the rack 44 to move proximally if the firing trigger 16 is released. FIG. 23 illustrates one embodiment of a spring stop 162. The spring stop 162 is coupled to the proximal end of the clamp spring 28.

Figure 24:
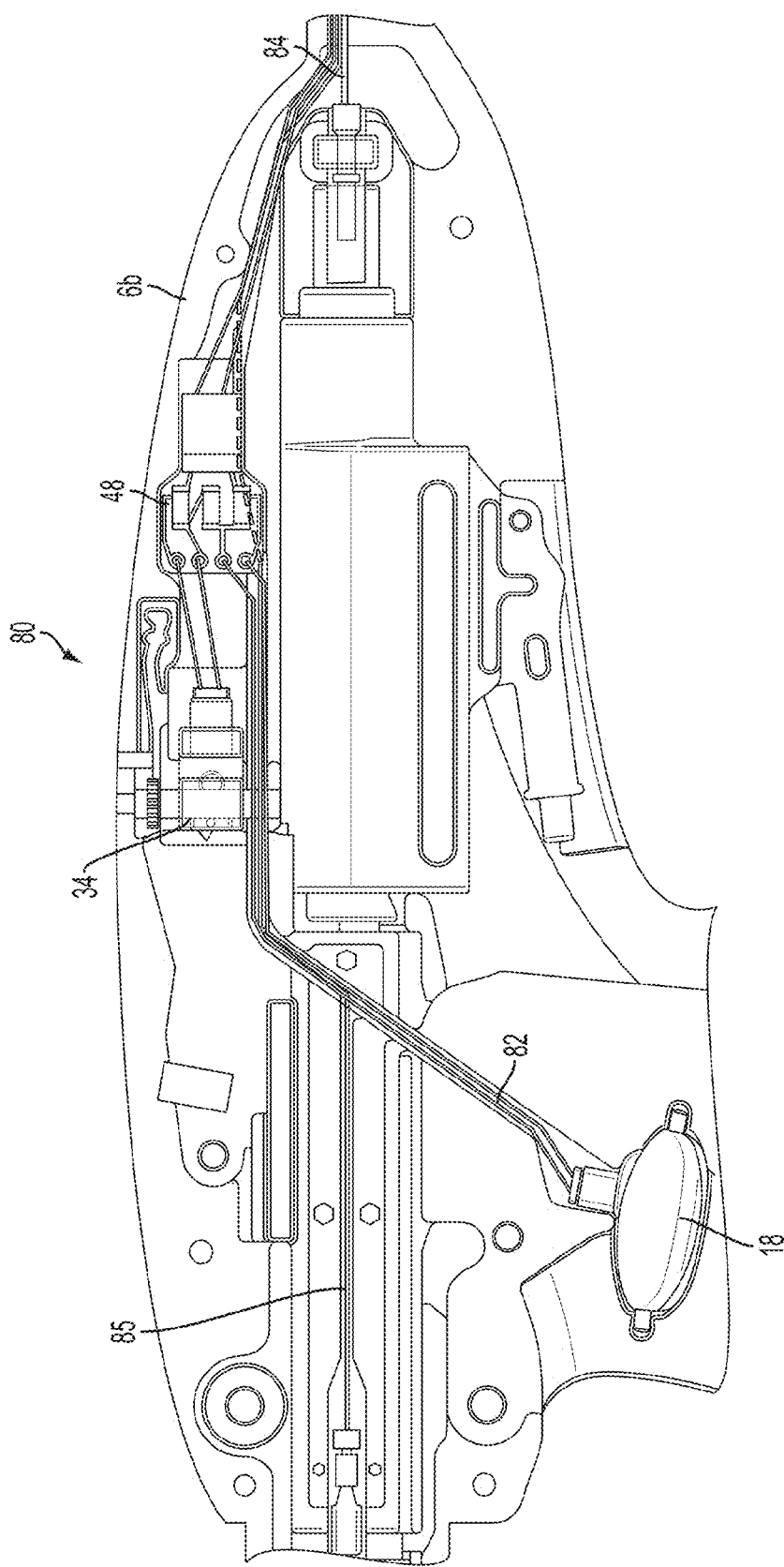
FIG. 24 illustrates one embodiment of an electrical energy system comprising an energy button, a source cable, and a return cable.

FIG. 24 illustrates one embodiment of an electrical energy system 80 mounted within the handle assembly 4. An energy button 18 is configured to deliver energy to an electrode 92 coupled to the end effector 10. The energy button 18 is coupled to a plurality of power activation wires 82. When the energy button 18 is depressed, a circuit is completed allowing delivery of energy to the electrode 92. A source path 84 couples an electrical contact mounted on the distal end of the outer tube 23 of the shaft assembly 12. In some embodiments, the source path comprises the outer tube 23. Alternatively, in some embodiments, the source path comprises a solid or stranded conductor housed within the outer tube 23. A return path 85 acts as a return for bipolar RF energy delivered to the electrode. For monopolar RF energy, the return path may comprise a grounding electrode coupled to a patient. In some embodiments, the power activation wires 82 are coupled to a generator. The control board 48 is further coupled to the jaw position switch 34 and the generator. The generator may prevent delivery of energy to the electrode 92 unless the jaw position sensor 34 indicates that the jaws 22a, 22b are in a sufficiently closed position.

Figure 25:
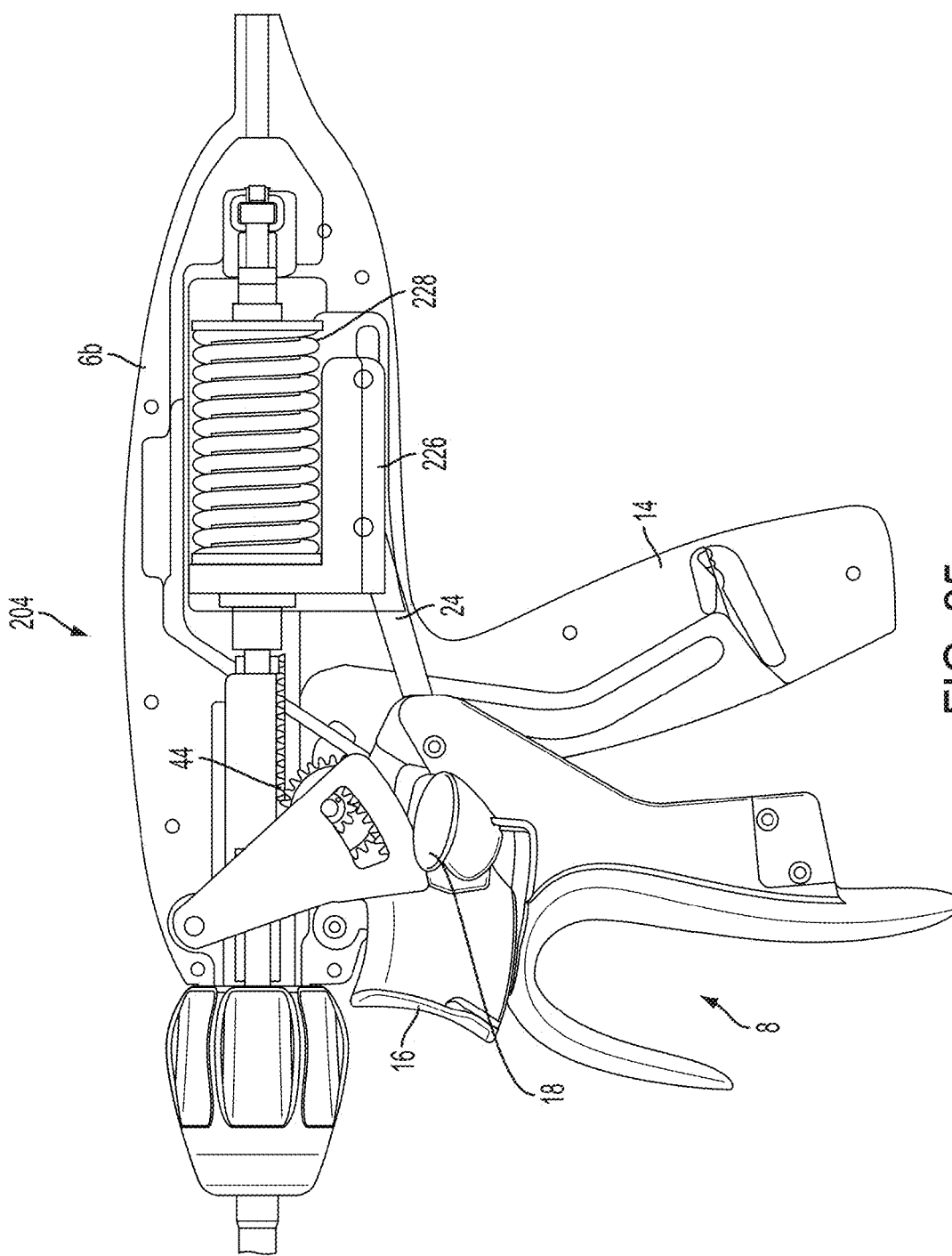
FIG. 25 illustrates one embodiment of an electrosurgical instrument comprising a pre-compressed jaw closure spring.

FIG. 25 illustrates one embodiment of an electrosurgical instrument 202 comprising a pre-compressed closure spring 228. The pre-compressed closure spring 228 comprises a closure spring having a certain pre-compression before actuation of the closure trigger 8. The pre-compressed closure spring 228 requires a clinician to apply less force to a closure trigger 8 to generate the same amount of force at the jaws 22a, 22b when compared to an un-compressed spring. The pre-compressed spring 228 may further provide a shorter stroke for compressing the jaws 22a, 22b to the same closure or force level as an uncompressed spring. The electrosurgical instrument 204 is otherwise similar to the electrosurgical instrument 4 discussed with respect to FIGS. 1-24. For example, closure of an end effector coupled to the surgical instrument 202 is affected by actuating a closure trigger 8 to move a yoke 226 proximally to compress the pre-compressed spring 228 and transition the jaws 22a, 22b from an open position to a closed position.

Figure 26:
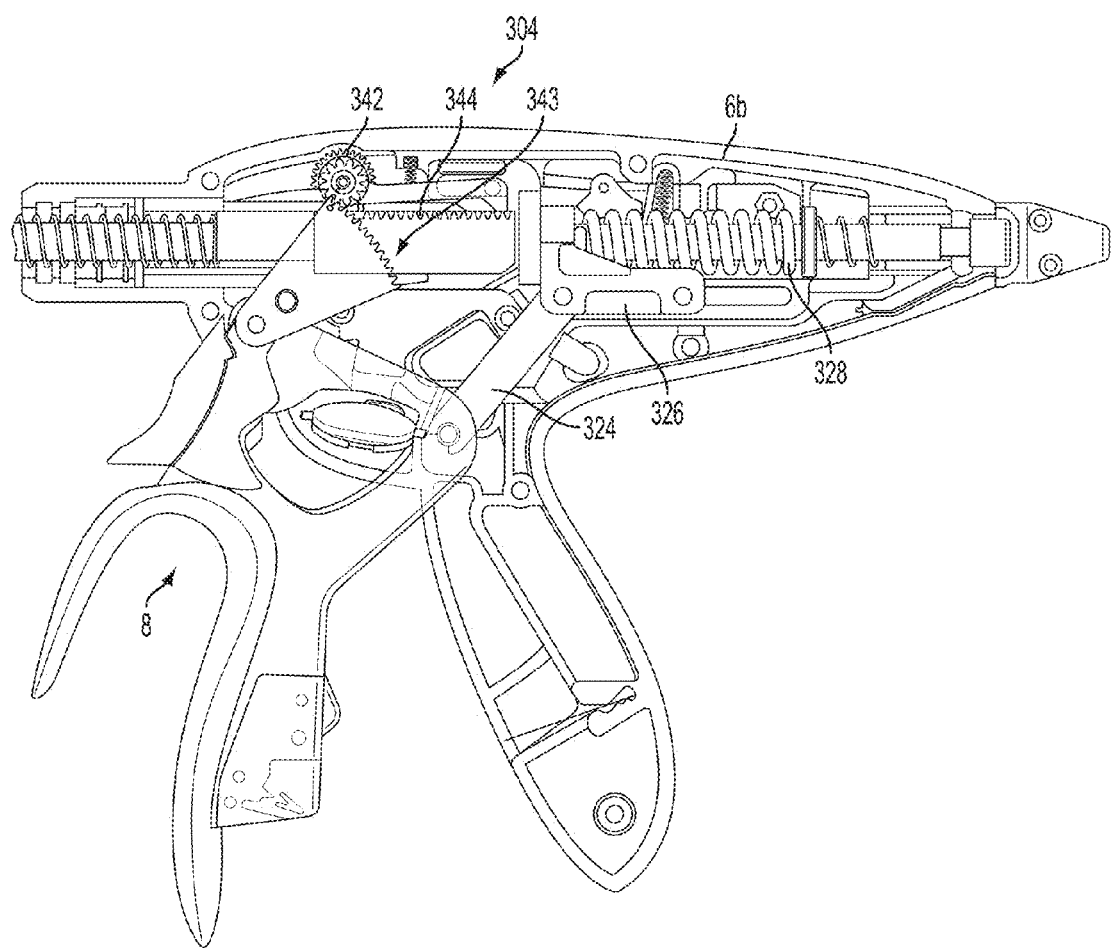
FIG. 26 illustrates one embodiment of an electrosurgical instrument comprising a top-mounted knife firing gear and rack.

FIG. 26 illustrates one embodiment of surgical instrument 302 comprising a handle assembly 304 having a top-mounted compound gear 342 and rack 344. The firing trigger 316 is coupled to the compound gear 342 by a plurality of teeth 343. Actuation of the firing trigger 316 advances the rack 344 in a distal direction. The rack 344 is coupled to a firing actuator (not illustrated) which advances a cutting member distally within an end effector coupled to the shaft 312. The surgical instrument 302 is otherwise similar to the electrosurgical instrument 4 illustrated in FIGS. 1-24. For example, closure of the jaws of an end effector coupled to the shaft assembly 312 is affected by actuating a closure trigger 8 coupled to a yoke 326 to compress a closure spring 328.

Figure 27A:
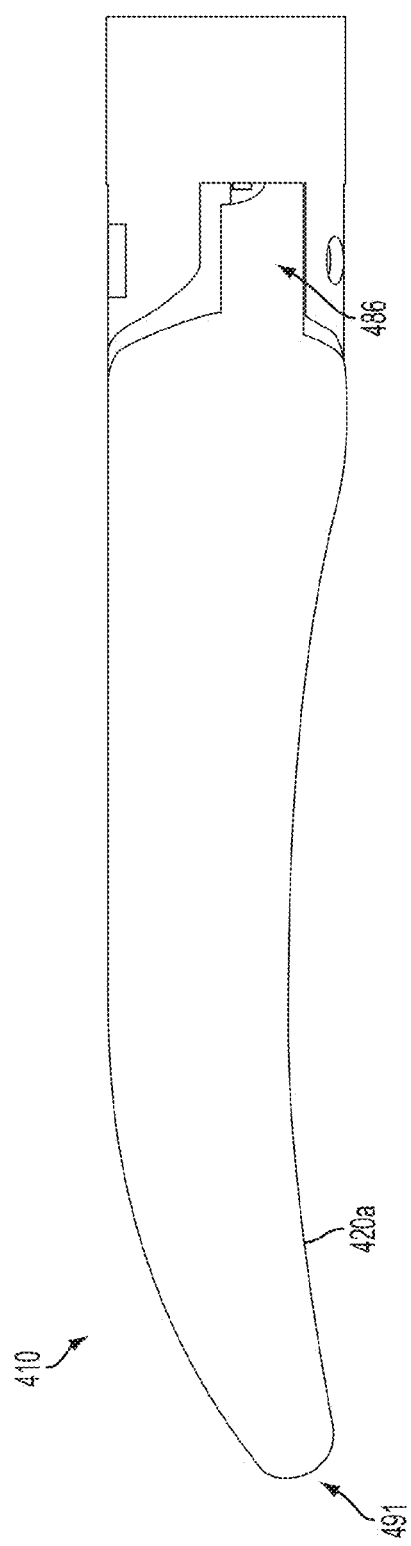
FIGS. 27A and 27B illustrate one embodiment of an electrosurgical end effector comprising a curved shape.
Figure 27B:
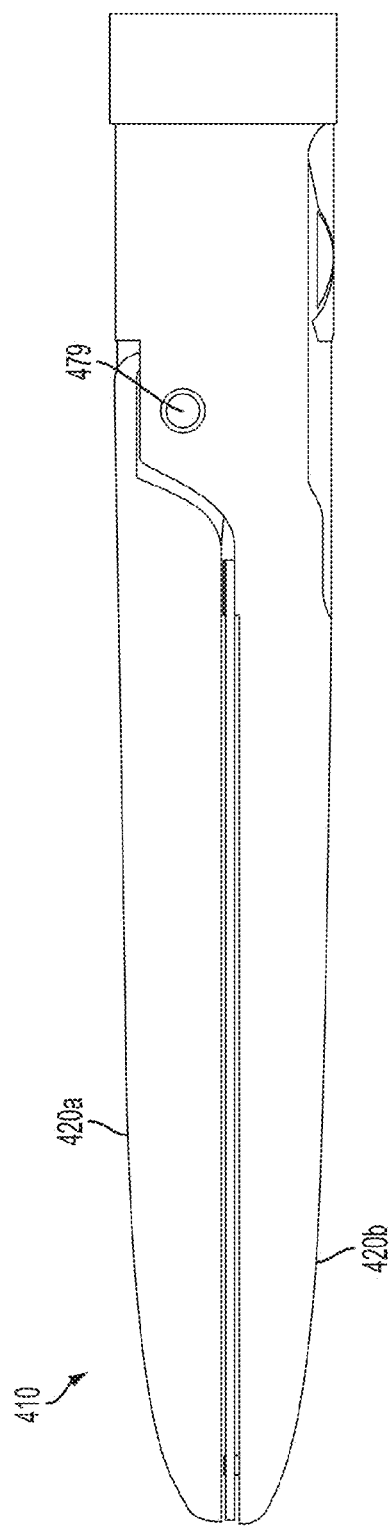

FIGS. 27A and 27B illustrate one embodiment of an electrosurgical end effector 410 comprising a curved shape. The end effector 410 comprises a first jaw member 422a and a second jaw member 422b. The first jaw member 422a is pivotally coupled by a pivot pin 479 to the second jaw member. The electrosurgical end effector 410 is configured to be coupled to an electrosurgical instrument, such as, for example, the electrosurgical instrument 2 illustrated in FIGS. 1-24. In some embodiments, the first jaw member 422a and the second jaw member 422b are smoothly tapered with the proximal portion of the jaw members 422a, 422b being the widest portion and the distal end of the jaw members 422a, 422b being the narrowest portion of the jaw members 422a, 422b. The smooth taper comprises a taper in a plane of curvature of the end effector 410 and parallel to a central axis of the shaft 412. For example, in some embodiments, the distal portion of the end effector 410 may comprise approximately 25% to 50% of the proximal width of the end effector 410, such as, for example, 33%. The smooth taper provides better dissection while maintaining a wide electrode through most of the end effector 410 for better sealing. The first jaw member 422a and the second jaw member 422b are curved along a longitudinal axis of the end effector 410. The curve of the end effector 410 comprises a radius of curvature. The radius of curvature may comprise, for example, a radius of about 1.000" to about 4.000".

The taper and curvature of the end effector 410 increase visibility of the tip 491. The taper compensates for the loss of force on the tissue on more proximal locations of the end effector 410 providing a more constant pressure on the tissue. The smooth transitions along the longitudinal axis of the end effector 410 and the taper distribute deflection along the length of the end effector 410 and reduce stress concentration allowing greater loads to be applied by the end effector 410. The reduced stresses and deflection permit the end effector 410 to be lengthened beyond non-curved, non-tapered end effectors. For example, in some embodiments, the end effector 410 comprises a length of approximately 23 mm.

In some embodiments, the end effector 410 comprises an offset pivot 486. The offset pivot 486 comprises a pivot point offset from the longitudinal axis of the shaft 412 and the end effector 410. The offset pivot enables the use of a linkage-style closure mechanism. The link pin 488 and offset pivot 486 provides precise control of the movement of the first jaw member 422a. FIG. 28 illustrates one embodiment of an end effector 510 comprising an offset pivot 586 coupled to an offset actuator. The offset actuator comprises a single asymmetric lever arm 590 coupled to the first jaw member 522a. The asymmetric lever arm 590 provides additional material around the pivot 586 when compared to a traditional two lever arm end effector.

Figure 29:
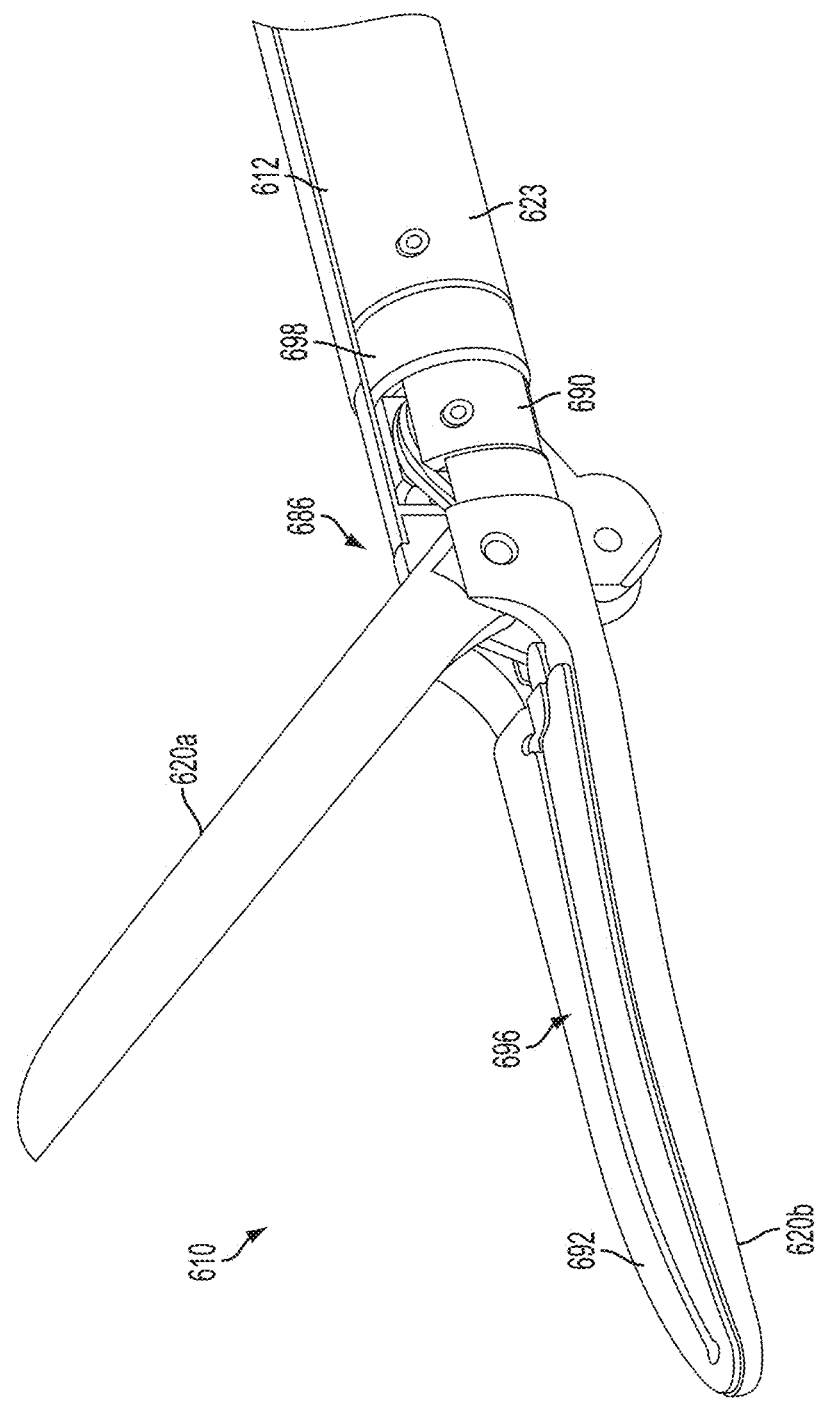
FIG. 29 illustrates one embodiment of an electrosurgical end effector comprising a first jaw member and a second jaw member having a smooth taper, curved shape.
Figure 30:
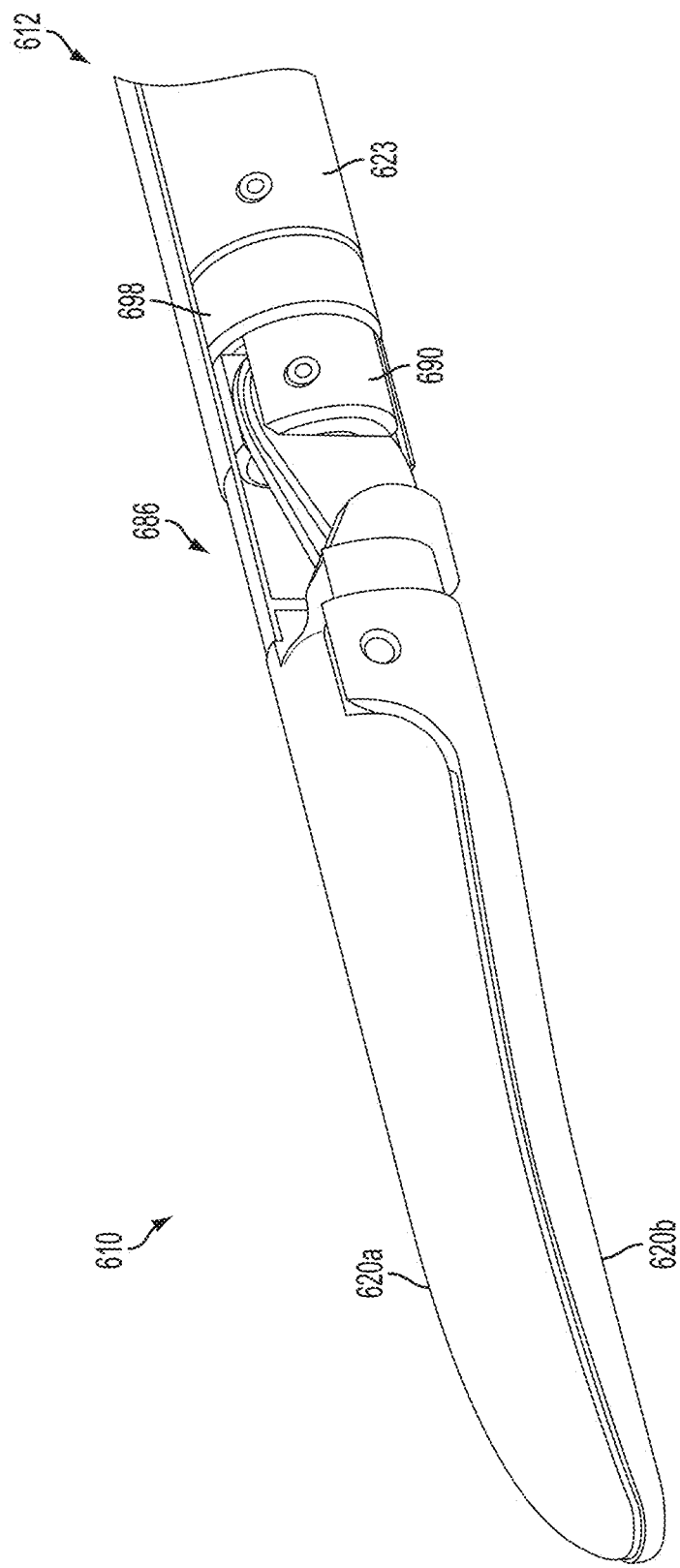
FIG. 30 illustrates one embodiment of the electrosurgical end effector of FIG. 29 in a closed position.

FIG. 29 illustrates one embodiment of an end effector 610 comprising an offset pivot 686 and an asymmetric lever arm 690 coupled to a shaft 612. The end effector 610 comprises a first jaw member 622a and a second jaw member 622b. The first jaw member 622a is pivotally moveable with respect to the second jaw member 622b. The second jaw member 622b is fixed. The first and second jaw members 622a, 622b comprises a curved shape having a radius of curvature with respect to a longitudinal axis of a shaft 612. The first jaw member 622a and the second jaw member 622b comprise a smooth taper from the proximal end to the distal end. The distal tip 690 comprises a width less than the width of the proximal section of the end effector 610. For example, in some embodiments, the distal tip comprises a width of about 25% to about 50% of the width of the proximal section of the end effector 610. The end effector 610 is illustrated in an open position in FIG. 29. In some embodiments, movement of the first jaw member 622a with respect to the second jaw member 622b is accomplished by a linked connection between the asymmetric lever arm 690 and an outer sheath 623 of the shaft 612. A low friction bushing 698, such as, for example, a lubricious metal or plastic, comprises a sliding interface between the asymmetric lever arm 690 and the outer sheath 623. The low friction bushing 698 is disposed between an outer diameter of the asymmetric lever arm 690 and an inner diameter of the shaft 612. FIG. 30 illustrates the end effector 610 of FIG. 29 in a closed position. As shown in FIG. 30, the end effector 610 is transitioned to a closed position by moving the asymmetric lever arm 690 proximally. Proximal movement of the asymmetric lever arm 690 may be affected by, for example, actuating a closure trigger 8 of a handle assembly 4 coupled to the end effector 610 by the shaft 612.

Figure 31:
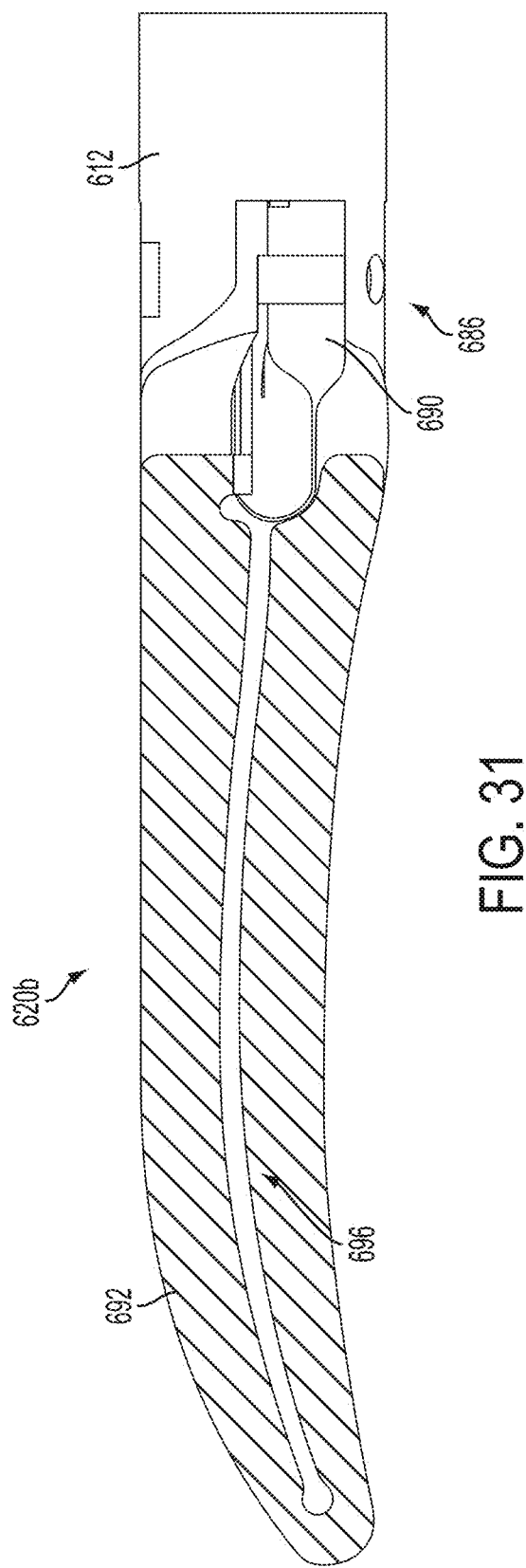
FIG. 31 illustrates one embodiment of a lower jaw of the electrosurgical end effector of FIGS. 29-30 comprising a curved longitudinal cutting member slot.

In some embodiments, an electrode 692 is coupled to the second jaw member 622b. The electrode 692 is adhered to the second jaw member 622b by an adhesive, such as, for example, a silicon or epoxy adhesive. The electrode 692 is selectively coated with a ceramic coating that provides electrical insulation to prevent shorting between the electrode 692 and the second jaw member 622b. In some embodiments, the ceramic coating and adhesive comprise a thermal conductivity of about 0.5 W/(mK) to about 2.0 W/(mK). The electrode 692 contacts a source electrode on the distal end of the outer tube 623 when the first jaw member 622a is rotated into a closed position with respect to the second jaw member 622b. Placement of the contact electrode on the outer shaft 623 ensures a good connection between the electrode 692 and an energy source. In some embodiments, the first jaw member 622a and/or the second jaw member 622b define a cutting member slot. FIG. 31 illustrates one embodiment of the second jaw member 622b comprising a cutting member slot 696. The proximal end of the cutting member slot 696 begins in a plane through a central axis of the shaft 612. The cutting member slot 696 biases to a first side of the central axis of the shaft 612 then crosses the central axis to a location biased to the opposite side of the central axis at the distal-most portion of the cutting member slot 696. The cutting member slot 696 shape maximizes the radius of the cutting member slot 696 reducing the bending load on the cutting member 695. The geometry of the cutting member slot 696 maintains a nearly equivalent electrode 692 width on both sides of the cutting member slot 696. In some embodiments, the curvature of the cutting member slot 696 is substantially equal to the curvature of the end effector 610, which is substantially equal to the curvature of the anatomy being transected. In some embodiments, a radius of curvature of the cutting member slot 696 varies from about 2.000" to about 4.000" over the length of the cutting member slot 696. In some embodiments, the cutting member slot 696 is biased to either the first side and/or the second side of the central axis of the shaft 612 by a distance of greater than 0.000" to a maximum of about 0.065".

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including"

should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

Various aspects of the subject matter described herein are set out in the following numbered clauses:

1. A surgical instrument comprising: a handle; a shaft assembly extending distally from the handle; an end effector coupled to a distal end of the shaft assembly, wherein the end effector comprises: a jaw assembly having a proximal end and a distal end, the jaw assembly comprising: a moveable jaw member; and a fixed jaw member, wherein the moveable jaw member is pivotably moveable between an open position and a closed position with respect to the fixed jaw member; wherein in the closed position, the jaw assembly defines a radius of curvature and a smooth taper from the proximal end to the distal end.

2. The surgical instrument of clause 1, wherein the distal end of the jaw assembly defines a width of between about 25% to about 50% of a width of a proximal end of the jaw assembly.

3. The surgical instrument of clause 2, wherein the smooth taper is configured to provide nearly constant pressure from a proximal end to a distal end of the jaw assembly.

4. The surgical instrument of clause 1, wherein the radius of curvature is about 1.000" to about 4.000".

5. The surgical instrument of clause 1, comprising a cutting member longitudinally deployable within a longitudinal curved slot defined by the jaw assembly, wherein the longitudinal curved slot comprises a proximal portion substantially in-line with a central axis of the shaft assembly, and wherein the longitudinal curved slot substantially follows the radius of curvature of the jaw assembly.

6. The surgical instrument of clause 5, wherein a central portion of the longitudinal curved slot is offset on a first side of the central axis of the shaft assembly by a distance of greater than 0.000" to about 0.065".

7. The surgical instrument of clause 6, wherein a distal portion of the longitudinal curved slot is offset on a second side of the central axis of the shaft assembly by a distance of greater than 0.000" to about 0.065".

8. The surgical instrument of clause 7, wherein the radius of curvature varies from about 2.000" to about 4.000".

9. The surgical instrument of clause 1, comprising a lever arm asymmetrically coupled to the moveable jaw member on a first side of a central axis of the shaft assembly, wherein the lever arm is configured to pivot the moveable jaw member from an open position to a closed position.

10. The surgical instrument of clause 9, wherein a pivot connection between the moveable jaw member and the fixed jaw member is offset to the first side of the axis of the shaft assembly.

11. The surgical instrument of clause 10, wherein the pivot connection comprises a pinned link-slider.

12. The surgical instrument of clause 9, wherein the lever arm extends longitudinally through the shaft assembly, and wherein a lubricous bushing is located between an outer diameter of the lever arm and an inner diameter of the shaft assembly.

13. The surgical instrument of clause 12, wherein the lubricous bushing comprises a plastic material.

14. The surgical instrument of clause 12, wherein the lubricous bushing comprises a dissimilar metal material.

15. The surgical instrument of clause 1, comprising an electrode disposed on the fixed jaw member, wherein the electrode is configured to deliver an electrosurgical radiofrequency (RF) signal.

16. The surgical instrument of clause 15, comprising a ceramic coating disposed on the electrode to electrically isolate the electrode from the fixed jaw member.

17. The surgical instrument of clause 16, wherein the ceramic coating comprises one of aluminum oxide or zirconium oxide.

18. The surgical instrument of clause 15, wherein the electrode is coupled to the fixed jaw member by an adhesive.

19. The surgical instrument of clause 18, wherein a thermal conductivity of the adhesive is approximately 0.5 W/(mK) to 2.0 W/(mK).

20. A surgical end effector, comprising: a jaw assembly having a proximal end and a distal end, the jaw assembly comprising: a moveable jaw member; a fixed jaw member; and a pivot connection coupling the moveable jaw member and the fixed jaw member, wherein the moveable jaw member is pivotably moveable between an open position and a closed position with respect to the fixed jaw member; wherein, in the closed position, the jaw assembly defines a radius of curvature and a smooth taper from the proximal end to the distal end.

21. The surgical end effector of clause 20, comprising a lever arm asymmetrically coupled to the first jaw member on a first side of a central axis of the jaw assembly, wherein the lever arm is configured to pivot the moveable jaw member from the open position to the closed position.

22. The surgical end effector of clause 21, wherein the pivot connection between the moveable jaw member and the fixed jaw member is offset to the first side of the axis of the jaw assembly.

23. The surgical end effector of clause 22, wherein the pivot connection comprises a pinned link-slider.

24. The surgical end effector of clause 21, comprising a lubricous bushing, wherein the lubricous bushing is configured to be located between an outer diameter of the lever arm and an inner diameter of an outer shaft when the end effector is coupled to a surgical instrument.

25. The surgical end effector of clause 24, wherein the lubricous bushing comprises a plastic material.

26. The surgical end effector of clause 24, wherein the lubricous bushing comprises a dissimilar metal material.

27. A surgical instrument comprising: a handle; a shaft assembly extending distally from the handle, the shaft assembly comprising a lever arm extending distally therethrough; an end effector coupled to a distal end of the shaft assembly, wherein the end effector comprises: a jaw assembly having a proximal end and a distal end, the jaw assembly comprising: a moveable jaw member; and a fixed jaw member, wherein the moveable jaw member is pivotably moveable between an open position and a closed position with respect to the fixed jaw member, wherein the lever arm is asymmetrically coupled to the moveable jaw member on a first side of a central axis of the shaft assembly, and wherein a pivot connection between the moveable jaw member and the fixed jaw member is offset to the first side of the central axis of the shaft assembly; wherein in the closed position, the jaw assembly defines a radius of curvature and a smooth taper from the proximal end to the distal end.

28. A surgical instrument comprising: a handle assembly comprising: a closure trigger defining an energy button hole; an energy button located within the energy button hole; a firing trigger; and a shaft assembly coupled to the handle assembly, the shaft assembly comprising: an outer tube; a closure actuator operatively coupled to the closure trigger; and a firing actuator operatively coupled to the firing trigger; and an end effector coupled to a distal end of the shaft assembly, the end effector comprising: a jaw assembly having a proximal end and a distal end, the jaw assembly comprising: a first jaw member; a second jaw member, wherein the first and second jaw members define a longitudinal slot, wherein the closure actuator is coupled to the first jaw member to pivotally move the first jaw member from an open position to a closed position relative to the second jaw member; and a cutting member deployable within the longitudinal slot, wherein the cutting member is coupled to the firing actuator to advance the cutting member distally within the longitudinal slot.

29. The surgical instrument of clause 28, wherein the handle assembly comprises: a compound gear coupled to the firing trigger, the compound gear comprising a high pivot; and a rack coupled to the firing actuator and operably coupled to the compound gear, wherein the compound gear is configured to rotate upon actuation of the firing trigger to advance the rack and firing actuator distally to deploy the cutting member distally within the end effector.

30. The surgical instrument of clause 29, wherein the firing actuator comprises a pull tube.

31. The surgical instrument of clause 29, wherein the handle assembly comprises a firing lock configured to prevent actuation of the firing trigger prior to closure of the jaw assembly, wherein the closure trigger is configured to release the firing lock when the closure trigger is in a predetermined closure position, and wherein release of the firing lock allows actuation of the firing trigger.

32. The surgical instrument of clause 31, wherein the handle assembly comprises a cutting member return spring stop comprising a crimp and a washer.

33. The surgical instrument of clause 28, wherein the closure trigger comprises a yoke interfaced with a closure spring, wherein the closure spring is coupled to the closure actuator, wherein actuation of the closure trigger slides the yoke proximally to compress the closure spring, and wherein compression of the closure spring moves the closure actuator proximally to rotate the first jaw member into a closed position.

34. The surgical instrument of clause 33, wherein the jaw closure spring comprises a pre-compressed spring.

35. The surgical instrument of clause 28, wherein the closure actuator comprises a lever arm asymmetrically coupled to the first jaw member, and wherein the jaw assembly comprises an offset pivot.

36. The surgical instrument of clause 28, wherein the shaft assembly comprises an electrical contact disposed on the outer tube and the end effector comprises an electrode, wherein the electrical contact is configured electrically couple the electrode to an energy source when the jaw assembly is in a closed position.

37. The surgical instrument of clause 1, wherein in the closed position, the jaw assembly defines a radius of curvature and a smooth taper from the proximal end to the distal end.

38. A surgical instrument comprising: a handle assembly comprising: a closure trigger defining an energy button hole; an energy button located within the energy button hole; and a firing trigger; a shaft assembly coupled to the handle assembly, the shaft assembly comprising: an outer tube; a closure actuator operatively coupled to the closure trigger; and a firing actuator operatively coupled to the firing trigger; and an end effector coupled to a distal end of the shaft assembly, the end effector comprising: a jaw assembly having a proximal end and a distal end, the jaw assembly comprising: a moveable jaw member; a fixed jaw member, wherein the moveable jaw member is pivotably moveable between an open position and a closed position with respect to the fixed jaw member, and wherein in the closed position, the jaw assembly defines a radius of curvature; and a cutting member deployable within the curved slot, wherein the cutting member is coupled to the firing actuator to advance the cutting member distally within the curved slot.

39. The surgical instrument of clause 38, wherein the handle assembly comprises: a compound gear coupled to the firing trigger, the compound gear comprising a high pivot; and a rack coupled to the firing actuator and operably coupled to the compound gear, wherein the compound gear is configured to rotate upon actuation of the firing trigger to advance the rack and firing actuator distally to deploy the cutting member distally within the end effector.

40. The surgical instrument of clause 38, wherein the firing actuator comprises a pull tube.

41. The surgical instrument of clause 40, wherein the handle assembly comprises a firing lock configured to prevent actuation of the firing trigger prior to closure of the jaw assembly, wherein the closure trigger is configured to release the firing lock when the closure trigger is in a predetermined closure position, and wherein release of the firing lock allows actuation of the firing trigger.

42. The surgical instrument of clause 41, wherein the handle assembly comprises a cutting member return spring stop comprising a crimp and a washer.

43. The surgical instrument of clause 38, wherein the closure trigger comprises a yoke interfaced with a closure spring, wherein the closure spring is coupled to the closure actuator, wherein actuation of the closure trigger slides the yoke proximally to compress the closure spring, and wherein compression of the closure spring moves the closure actuator proximally to rotate the first jaw member into a closed position.

44. The surgical instrument of clause 43, wherein the jaw closure spring comprises a pre-compressed spring.

45. The surgical instrument of clause 38, wherein the shaft assembly comprises an electrical contact disposed on the outer tube and the end effector comprises an electrode, wherein the electrical contact is configured electrically couple to the end effector when the jaw assembly is in a closed position.

46. The surgical instrument of clause 38, wherein in the closed position the jaw assembly comprising smooth taper from the proximal end to the distal end.

47. A surgical instrument comprising: a handle assembly comprising: a closure trigger defining an energy button hole; an energy button located within the energy button hole; and a firing trigger; a shaft assembly coupled to the handle assembly, the shaft assembly comprising: an outer tube; a closure actuator operatively coupled to the closure trigger; and a firing actuator operatively coupled to the firing trigger; and an end effector coupled to a distal end of the shaft assembly, the end effector comprising: a jaw assembly having a proximal end and a distal end, the jaw assembly comprising: a moveable jaw member; and a fixed jaw member, wherein the moveable jaw member is pivotably moveable between an open position and a closed position with respect to the fixed jaw member, wherein the closure actuator is asymmetrically coupled to the moveable jaw member on a first side of a central axis of the shaft assembly, and wherein a pivot connection between the moveable jaw member and the fixed jaw member is offset to the first side of the central axis of the shaft assembly; wherein in the closed position, the jaw assembly defines a radius of curvature and a smooth taper from the proximal end to the distal end.

What is claimed is:

1. A surgical instrument comprising:
   a handle assembly comprising:
      a first handle housing located on a first side of the handle assembly and a second handle housing located on a second and opposing side of the handle assembly;
      a closure trigger defining an energy button hole;
      an energy button comprising a first end and a second end located within the energy button hole and extending through the handle assembly, wherein the first energy button end is accessible from the first handle housing and the second energy button end is accessible from the second handle housing; and
      a firing trigger;
   a shaft assembly coupled to the handle assembly, the shaft assembly comprising:
      an outer tube;
      a closure actuator operatively coupled to the closure trigger; and
      a firing actuator operatively coupled to the firing trigger; and
   an end effector coupled to a distal end of the shaft assembly, the end effector comprising:
      a jaw assembly having a proximal end and a distal end, the jaw assembly comprising:
         a first jaw member; and
         a second jaw member, wherein the first and second jaw members define a longitudinal slot, wherein the closure actuator is coupled to the first jaw member to pivotally move the first jaw member from an open position to a closed position relative to the second jaw member; and
      a cutting member deployable within the longitudinal slot, wherein the cutting member is coupled to the firing actuator to advance the cutting member distally within the longitudinal slot.

2. The surgical instrument of claim 1, wherein the handle assembly comprises:
   a compound gear coupled to the firing trigger, the compound gear comprising a high pivot; and
   a rack coupled to the firing actuator and operably coupled to the compound gear, wherein the compound gear is configured to rotate upon actuation of the firing trigger to advance the rack and firing actuator distally to deploy the cutting member distally within the end effector.

3. The surgical instrument of claim 2, wherein the firing actuator comprises a pull tube.

4. The surgical instrument of claim 2, wherein the handle assembly comprises a firing lock configured to prevent actuation of the firing trigger prior to closure of the jaw assembly, wherein the closure trigger is configured to release the firing lock when the closure trigger is in a predetermined closure position, and wherein release of the firing lock allows actuation of the firing trigger.

5. The surgical instrument of claim 4, wherein the handle assembly comprises a cutting member return spring stop comprising a crimp and a washer.

6. The surgical instrument of claim 1, wherein the closure trigger comprises a yoke interfaced with a closure spring, wherein the closure spring is coupled to the closure actuator, wherein actuation of the closure trigger slides the yoke proximally to compress the closure spring, and wherein compression of the closure spring moves the closure actuator proximally to rotate the first jaw member into a closed position.

7. The surgical instrument of claim 6, wherein the j-aw closure spring comprises a pre-compressed spring.

8. The surgical instrument of claim 1, wherein the closure actuator comprises a lever arm asymmetrically coupled to the first jaw member, and wherein the jaw assembly comprises an offset pivot.

9. The surgical instrument of claim 1, wherein the shaft assembly comprises an electrical contact disposed on the outer tube and the end effector comprises an electrode, wherein the electrical contact is configured to electrically couple the electrode to an energy source when the jaw assembly is in a closed position.

10. The surgical instrument of claim 1, wherein in the closed position, the jaw assembly defines a radius of curvature and a smooth taper from the proximal end to the distal end.

11. A surgical instrument comprising:
a handle assembly comprising:
  a first handle housing located on a first side of the handle assembly and a second handle housing located on a second and opposing side of the handle assembly;
  a closure trigger defining an energy button hole;
  an energy button comprising a first end and a second end located within the energy button hole and extending through the handle assembly, wherein the first energy button end is accessible from the first handle housing and the second energy button end is accessible from the second handle housing; and
  a firing trigger;
a shaft assembly coupled to the handle assembly, the shaft assembly comprising:
  an outer tube;
  a closure actuator operatively coupled to the closure trigger; and
  a firing actuator operatively coupled to the firing trigger; and
an end effector coupled to a distal end of the shaft assembly, the end effector comprising:
  a jaw assembly having a proximal end and a distal end, the jaw assembly comprising:
    a moveable jaw member; and
    a fixed jaw member, wherein the moveable jaw member is pivotably moveable between an open position and a closed position with respect to the fixed jaw member, and wherein in the closed position, the jaw assembly defines a radius of curvature; and
  a cutting member deployable within a curved slot, wherein the cutting member is coupled to the firing actuator to advance the cutting member distally within the curved slot.

12. The surgical instrument of claim 11, wherein the handle assembly comprises:
a compound gear coupled to the firing trigger, the compound gear comprising a high pivot; and
a rack coupled to the firing actuator and operably coupled to the compound gear, wherein the compound gear is configured to rotate upon actuation of the firing trigger to advance the rack and firing actuator distally to deploy the cutting member distally within the end effector.

13. The surgical instrument of claim 11, wherein the firing actuator comprises a pull tube.

14. The surgical instrument of claim 13, wherein the handle assembly comprises a firing lock configured to prevent actuation of the firing trigger prior to closure of the jaw assembly, wherein the closure trigger is configured to release the firing lock when the closure trigger is in a predetermined closure position, and wherein release of the firing lock allows actuation of the firing trigger.

15. The surgical instrument of claim 12, wherein the handle assembly comprises a cutting member return spring stop comprising a crimp and a washer.

16. The surgical instrument of claim 11, wherein the closure trigger comprises a yoke interfaced with a closure spring, wherein the closure spring is coupled to the closure actuator, wherein actuation of the closure trigger slides the yoke proximally to compress the closure spring, and wherein compression of the closure spring moves the closure actuator proximally to rotate the first jaw member into a closed position.

17. The surgical instrument of claim 16, wherein the closure spring comprises a pre-compressed spring.

18. The surgical instrument of claim 11, wherein the shaft assembly comprises an electrical contact disposed on the outer tube and the end effector comprises an electrode, wherein the electrical contact is configured to electrically couple to the end effector when the jaw assembly is in a closed position.

19. The surgical instrument of claim 11, wherein in the closed position the jaw assembly comprises smooth taper from the proximal end to the distal end.

20. A surgical instrument comprising:
a handle assembly comprising:
  a first handle housing located on a first side of the handle assembly and a second handle housing located on a second and opposing side of the handle assembly;
  a closure trigger defining an energy button hole;
  an energy button comprising a first end and a second end located within the energy button hole and extending through the handle assembly, wherein the first energy button end is accessible from the first handle housing and the second energy button end is accessible from the second handle housing; and
  a firing trigger;
a shaft assembly coupled to the handle assembly, the shaft assembly comprising:
  an outer tube;
  a closure actuator operatively coupled to the closure trigger; and
  a firing actuator operatively coupled to the firing trigger; and
an end effector coupled to a distal end of the shaft assembly, the end effector comprising:
  a jaw assembly having a proximal end and a distal end, the jaw assembly comprising:
    a moveable jaw member; and
    a fixed jaw member, wherein the moveable jaw member is pivotably moveable between an open position and a closed position with respect to the fixed jaw member, wherein the closure actuator is asymmetrically coupled to the moveable jaw member on a first side of a central axis of the shaft assembly, and wherein a pivot connection between the moveable jaw member and the fixed jaw member is offset to the first side of the central axis of the shaft assembly;
  wherein in the closed position, the jaw assembly defines a radius of curvature and a smooth taper from the proximal end to the distal end.

* * * * *